(12) United States Patent
Xie

(10) Patent No.: US 11,583,594 B2
(45) Date of Patent: Feb. 21, 2023

(54) PERSONALIZED MEDICINE THERAPEUTIC MINICIRCLE

(71) Applicant: Syno Minicircle Biotechnology Co. Ltd., Shenzhen (CN)

(72) Inventor: Yiwu Xie, Shenzhen (CN)

( * ) Notice: Subject to any disclaimer, the term of this patent is extended or adjusted under 35 U.S.C. 154(b) by 0 days.

(21) Appl. No.: 15/640,577

(22) Filed: Jul. 2, 2017

(65) Prior Publication Data

US 2018/0296699 A1 Oct. 18, 2018

(51) Int. Cl.
| | | |
|---|---|---|
| A61K 48/00 | (2006.01) | |
| C07K 16/46 | (2006.01) | |
| C07K 16/28 | (2006.01) | |
| A61K 39/395 | (2006.01) | |
| C07K 16/26 | (2006.01) | |
| C07K 16/30 | (2006.01) | |
| C07K 14/725 | (2006.01) | |
| A61K 39/00 | (2006.01) | |

(52) U.S. Cl.
CPC ...... *A61K 48/0008* (2013.01); *A61K 39/3955* (2013.01); *A61K 48/0033* (2013.01); *A61K 48/0041* (2013.01); *A61K 48/0058* (2013.01); *A61K 48/0075* (2013.01); *A61K 48/0091* (2013.01); *C07K 14/7051* (2013.01); *C07K 16/26* (2013.01); *C07K 16/28* (2013.01); *C07K 16/2803* (2013.01); *C07K 16/283* (2013.01); *C07K 16/2809* (2013.01); *C07K 16/2869* (2013.01); *C07K 16/2887* (2013.01); *C07K 16/30* (2013.01); *C07K 16/3069* (2013.01); *C07K 16/468* (2013.01); *A61K 2039/53* (2013.01); *C07K 2317/31* (2013.01); *C07K 2317/569* (2013.01); *C07K 2317/622* (2013.01); *C07K 2317/76* (2013.01); *C12N 2800/10* (2013.01)

(58) Field of Classification Search
CPC ............ A61K 2039/53; A61K 39/3955; A61K 48/0008; A61K 48/0033; A61K 48/0041; A61K 48/0058; A61K 48/0075; A61K 48/0091; C07K 14/7051; C07K 16/26; C07K 16/28; C07K 16/2803; C07K 16/2809; C07K 16/283; C07K 16/2869; C07K 16/2887; C07K 16/30; C07K 16/3069; C07K 16/468; C07K 2317/31; C07K 2317/569; C07K 2317/622; C07K 2317/76; C12N 2800/10
USPC ........ 435/69.6, 320.1, 325, 328, 372.3, 375, 435/455; 424/93.21, 450
See application file for complete search history.

(56) References Cited

U.S. PATENT DOCUMENTS

| | | | |
|---|---|---|---|
| 2006/0188988 A1* | 8/2006 | Draghia-Akli | A61K 38/25 435/455 |
| 2011/0118333 A1* | 5/2011 | Wu | C12N 15/85 514/44 A |
| 2016/0280795 A1* | 9/2016 | Wang | C07K 16/2809 |
| 2016/0312230 A1* | 10/2016 | Chen | C12N 15/10 |
| 2018/0230225 A1* | 8/2018 | Fan | C07K 16/30 |

OTHER PUBLICATIONS

Chen et al. Human Gene Therapy 16:126-131 (Jan. 2005) (Year: 2005).*
Chabot et al., Chapter 12, pp. 203-213. Minicircle and Miniplasmid DNA Vectors : The Future of Non-Viral and Viral Gene Transfer, edited by Martin Schleef, John Wiley & Sons, Incorporated, 2013. (Year: 2013).*
Zhdanov et al. Methods in Enzymology, vol. 373, Chapter 28, pp. 433-465. (Year: 2003).*

* cited by examiner

*Primary Examiner* — Janet L Epps-Smith
(74) *Attorney, Agent, or Firm* — Bioinnovation Legal PLLC; James C. Schroeder

(57) ABSTRACT

Bispecific antibodies (bsAbs) have emerged as a class of promising anti-cancer and anti-infection biological drugs. They are capable of killing target cells, either cancer cells or microbe-infected cells, at levels of nanograms per milliliter serum in vivo, about 1e+5 folds more powerful than regular antibodies. To bypass the problems of high cost in production and inconvenience in administration, a logical solution is to use gene therapy vectors to produce them in vivo. In a series of preclinical studies, we have demonstrated that DNA MiniCircle was able to express far above therapeutic levels of bsAB persistently both in the presence as well as the absence of transfection co-factors. As a specific and intended improvement of the claimed invention, an enhanced form of bispecific antibodies incorporating a target cell-effector cell bridging device (BTEC) is additionally disclosed.

3 Claims, 11 Drawing Sheets
Specification includes a Sequence Listing.

101

201

PERSONALIZED MEDICINE THERAPEUTIC MINICIRCLE

RELATED APPLICATIONS

This application claims priority to China Application Number 201710245146.6 filed on Apr. 14, 2017.

TECHNICAL FIELD

The claimed invention and embodiments thereof relate to medical applications for circularized DNA regions. With greater particularity, the disclosed embodiments for MiniCircle DNA enhance therapeutic uptake and production of therapeutic multi-modal regions encoded by circularized DNA regions.

BACKGROUND ART

While direct administration of DNA for therapeutic purposes has been previously investigated, the successful administration of DNA for therapeutic purposes has been elusive. Attempts to utilize traditional plasmids via direct administration for therapeutic purposes have been problematic at best and have met with limited success by the scientific and medical community for over a quarter century. While transgene products expressed by intramuscular injection of plasmids was first reported in 1990, constant efforts to turn muscle into a factory of therapeutic gene products have met with limited success and not been effective from a therapeutic or cost perspective.

SUMMARY OF INVENTION

Technical Problem

When utilizing traditional plasmids for direct delivery of therapeutic gene products, plasmid backbone DNA results in silencing of transgene expression in body tissue such as muscle and liver. With intramuscularly injected regular plasmids, transgene expression is transient at best and neither stable nor sustainable. To overcome the silencing effect of plasmids in vivo, an alternate approach to plasmid delivery is needed and required for therapeutic delivery of DNA in the body. Moreover, new therapeutic approaches are needed beyond simple monoclonal antibodies.

Solution to Problem

In side-by-side experiments, transgene expression of plasmid DNA declines sharply when compared with engineered DNA MiniCircle used as a vector for delivery. As demonstrated in the illustrative embodiments, engineering circularized DNA for therapeutic administration of useful gene groups avoids the DNA silencing effect clearly present from plasmid DNA delivery. Further improvements over plasmid delivery of therapeutic gene groups of interest are obtained through consideration of administration target location as well as the presence or express absence of transfection co-factors.

Enhancements include tissue specificity when administering circularized DNA for therapeutic purposes. By selecting muscle tissue as the target site for in vivo administration, MiniCircle DNA delivered to muscle is able to express gene products more consistently and at a more stable rate than other locations. Alternate embodiments of the claimed invention include the presence as well as the absence of transfection co-factors such as glycyrrhizin (GL), Gensing Rh1 (GS), polyvinylpyrrolidone (PVP) and polyethyl glycol (PEG) to enhance MiniCircle transfection efficiency. In a noteworthy and unexpected embodiment of the claimed invention, administration of the DNA MiniCircle alone without transfection aids additionally demonstrates a substantial therapeutic improvement in transgene expression.

Additional enhancements are obtained through the rational redesign of the circularized DNA MiniCircle to express a functional Bridge between Target and Effector Cells (BTEC) not only to incorporate bispecific antibodies but also to include broader cell bridging functionality. BTEC (the Bridge between Target and Effector Cells) is an engineered protein comprising two arms or parts: one arm recognizing target cells, the other arm recognizing effector cells via binding to the molecules on T (or NK) cell receptor signaling pathway. The BTEC can redirect the effector cells to the target cells and consequently lead to specific T (or NK) cells cytotoxicity on target cells.

Advantageous Effects of Invention

Advantageous effects of the claimed invention include novel approaches to delivery of therapeutic gene groups in vivo. In a direct and foreseen illustrative embodiment of the claimed invention, bi-specific antibodies are generated as a result of successful MiniCircle DNA delivery to a specific body tissue such as muscle. In a further illustrative embodiment of the claimed invention, bi-specific antibodies are generated via MiniCircle DNA delivery in a sustained and therapeutic release for the administration and treatment of cancer wherein traditional plasmid delivery would not be sustained. Additional embodiments illustrate the advantageous effects of bridging target and effector cells resulting in new and improved therapeutic applications.

BRIEF DESCRIPTION OF DRAWINGS

The accompanying drawings are included to better illustrate exemplary embodiments of the claimed invention.

DESCRIPTION OF EMBODIMENTS

In the following embodiments as detailed further in the corresponding figures, enhanced in vivo therapeutic genetic material delivery via MiniCircle are detailed in the presence and absence of transfection co-factors. Additional embodiments illustrate the rational redesign of MiniCircle DNA to create an effective Bridge between Target and Effector Cells (BTEC) for therapeutic applications.

EXAMPLES

In the first and second illustrative examples of the claimed invention, efficacy of MiniCircle transfection in the presence and absence of a transfection co-factor is illustrated utilizing glycyrrhinzin (GL). In the illustrative figures the illustrative glycyrrhinzin (GL) co-factor is identified as MusFX. While glycyrrhinzin (GL) is utilized as an illustration, it is a direct and intended consequence of the claimed invention to utilize other co-factors such as Gensing Rh1 (GS), and polyethyl glycol (PEG) to enhance MiniCircle transfection efficiency as well as transfecting in the absence of a co-factor as well. More broadly considered, any chemical comprising a hydrophobic core and a sugar moiety can be capable of enhancing MiniCircle transfection.

Figure 1:
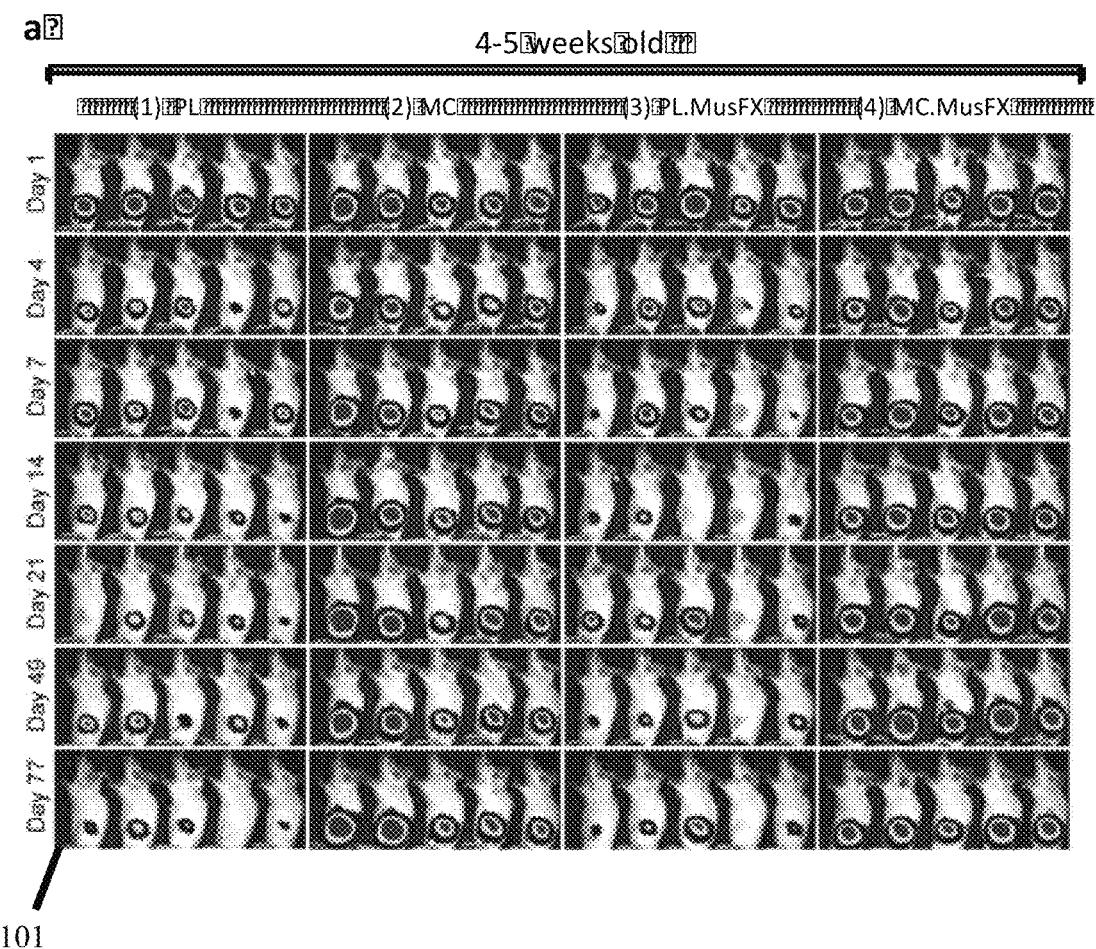
FIG. 1 is an illustrative biofluorescence image demonstrating plasmid backbone DNA silencing effect in Female BABL/C mice at 4-5 weeks of age.
Figure 2:
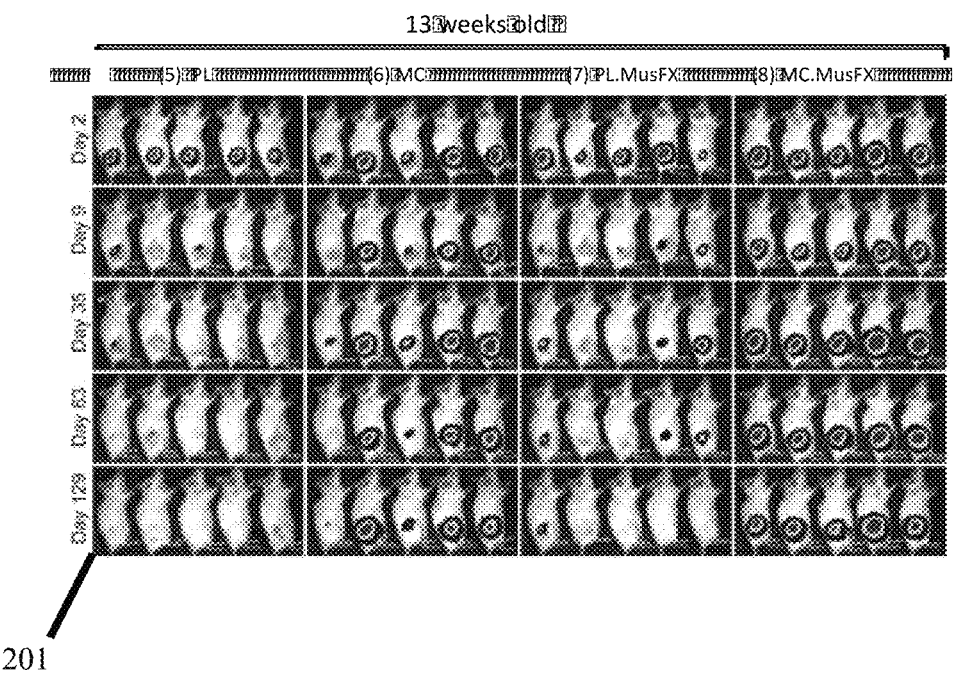
FIG. 2 is an illustrative biofluorescence image demonstrating plasmid backbone DNA silencing effect in Female BABL/C mice at 13 weeks of age.
Figure 3:
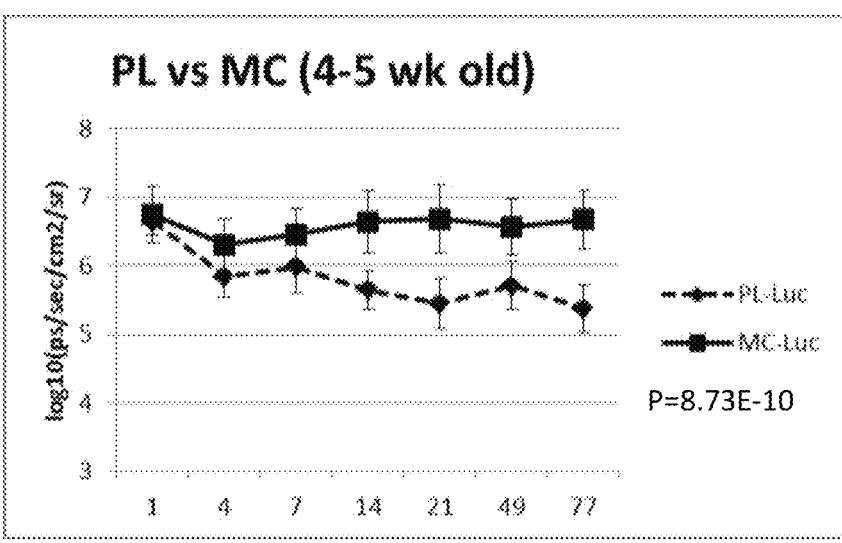
FIG. 3 is a graphical chart illustrating luciferase quantity of Plasmid vs MiniCircle.
Figure 4:
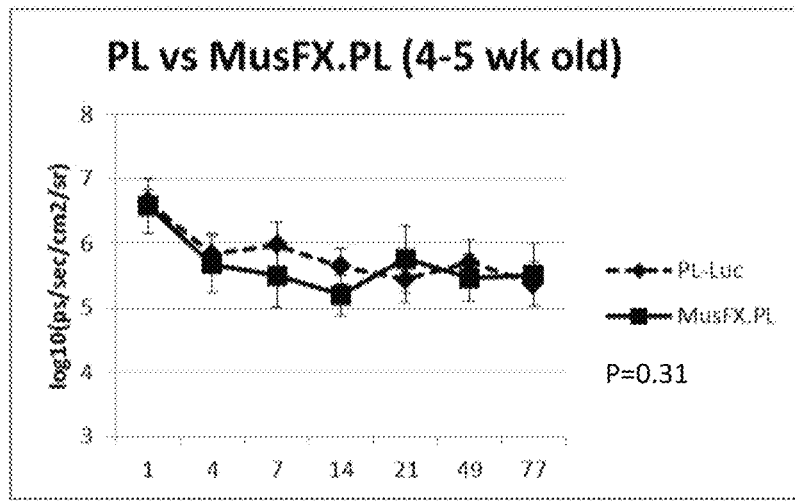
FIG. 4 is a graphical chart illustrating luciferase quantity of Plasmid vs MusFX.Plasmid.
Figure 5:
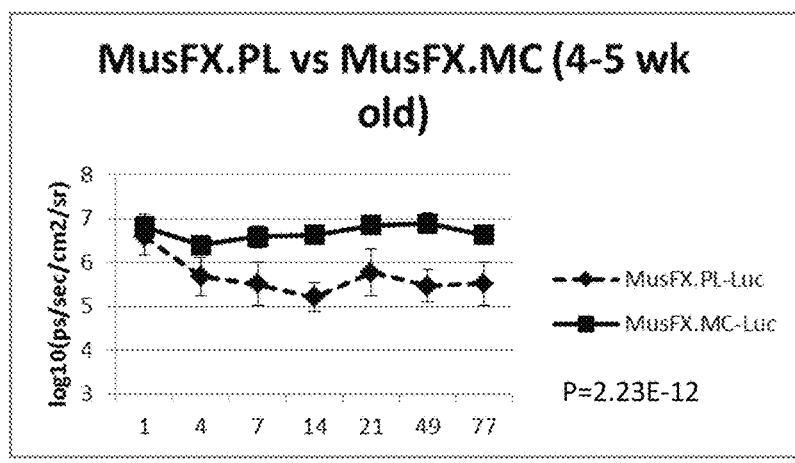
FIG. 5 is a graphical chart illustrating luciferase quantity of MusFX.Plasmid vs MusFX.MiniCircle.
Figure 6:
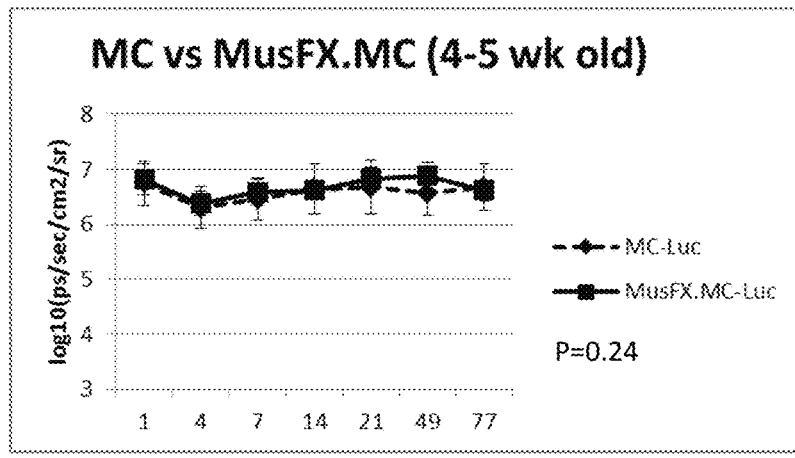
FIG. 6 is a graphical chart illustrating luciferase quantity of MiniCircle vs MusFX.MiniCircle.
Figure 7:
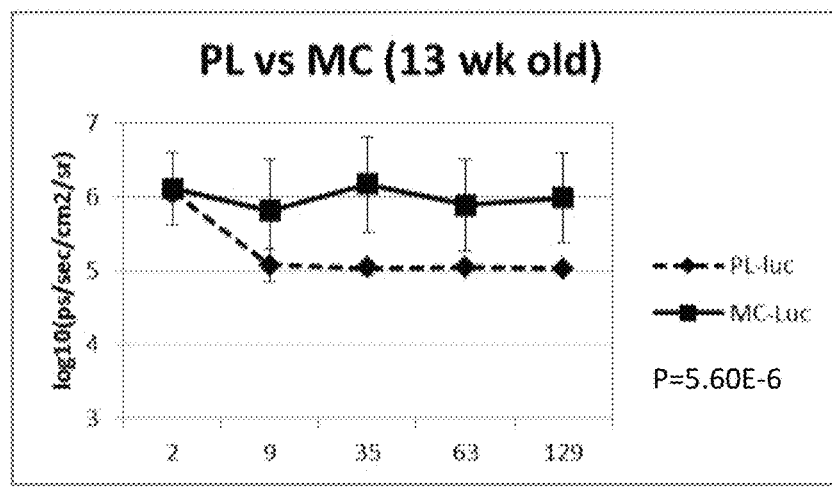
FIG. 7 is a graphical chart illustrating luciferase quantity of Plasmid vs MiniCircle.
Figure 8:
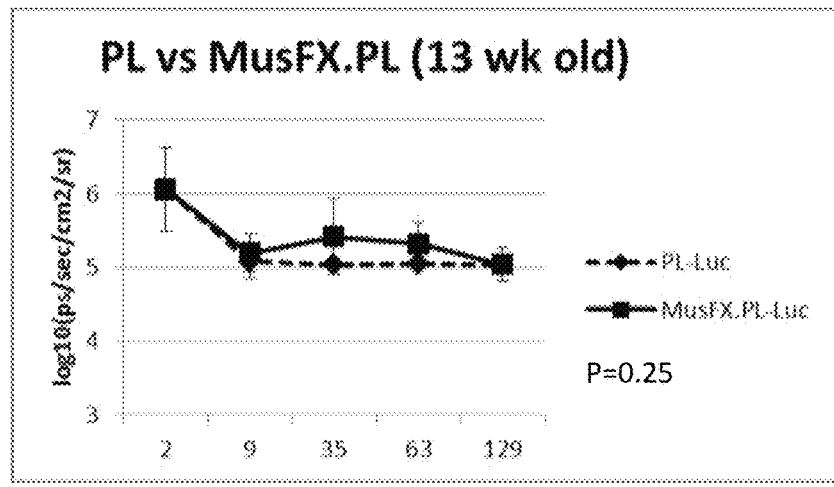
FIG. 8 is a graphical chart illustrating luciferase quantity of Plasmid vs MusFX.Plasmid.
Figure 9:
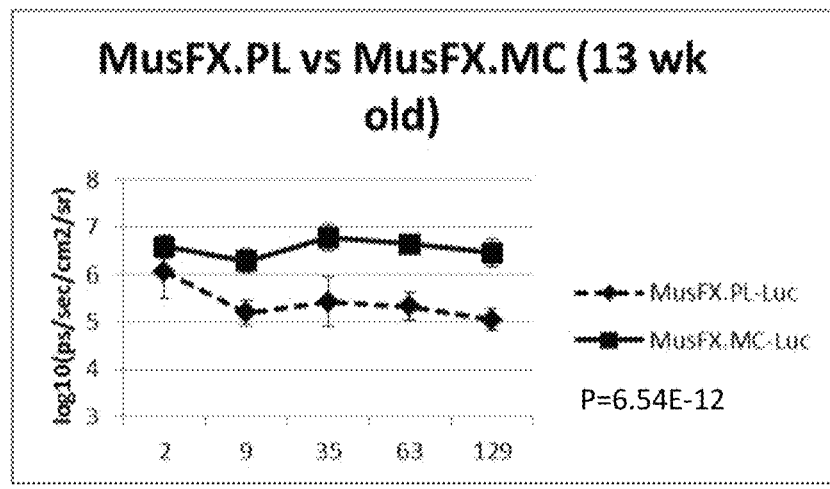
FIG. 9 is a graphical chart illustrating luciferase quantity of MusFX.Plasmid vs MusFX.MiniCircle.
Figure 10:
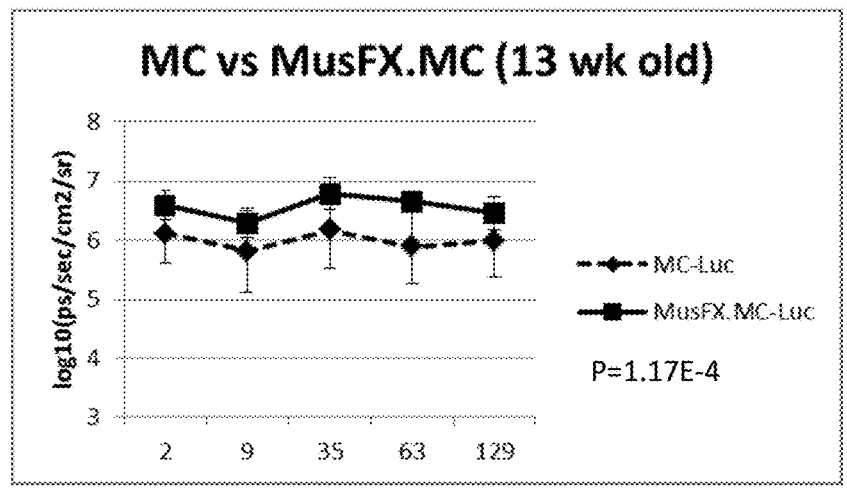
FIG. 10 is a graphical chart illustrating luciferase quantity of MiniCircle vs MusFX.MiniCircle.

FIG. 1 and FIG. 2 demonstrate plasmid backbone DNA silencing effect as illustrated in biofluorescence image. Female BABL/C mice of 4-5- or 13 weeks of age are divided into 4 groups each age, and are treated with standard plasmid (PL), mincircle (MC), PL plus MusFX (MusFX-PL), or MC plus MusFX. Both plasmid and MC encoded the same luciferase gene. Each mouse is injected at quadriceps muscle a dose of DNA mix comprising 50-μl of PBS, 3-μg of MC or eqimolar amount of PL, with or without 1.74 μg of MusFX. Biofluorescence of luciferase of individual mouse from injected DNA vector is measured periodically. n=5 for all groups except FIG. 6 where two mice are triaged because of poor injection. FIGS. 3-10 represent graphical chart representation of luciferase quantity. The chart is derived from the measurement of biofluorescence image. Statistically significant difference in luciferase biofluorescence is at $p<0.01$ between the groups in the chart of 3, 5, 7, 9 and 10.

Example 1

FIG. 1 is an illustrative biofluorescence image demonstrating plasmid backbone DNA silencing effect in Female BABL/C mice at 4-5 weeks of age. Image panel 101 depicts varying levels of gene expression indicating transfection efficiency by contrasting plasmid (PL), MiniCircle alone (MC), Plasmid with co-transfection agent MusFX (PL, MusFX) and MiniCircle with co-transfection agent MusFX (MC, MusFX). FIGS. 3-6 are graphical depictions charting corresponding differences between gene expression levels of plasmid and MiniCircle in the presence and absence of transfection co-factor Mus.FX at 4-5 weeks. As FIG. 3 clearly illustrates, gene expression levels from transfection of MiniCircle alone result in a clear superiority over transfecting the same gene group utilizing a plasmid vector.

Example 2

FIG. 2 is an illustrative biofluorescence image demonstrating plasmid backbone DNA silencing effect in Female BABL/C mice at 13 weeks of age. Image panel 101 depicts varying levels of gene expression indicating transfection efficiency by contrasting plasmid (PL), MiniCircle alone (MC), Plasmid with co-transfection agent MusFX (PL, MusFX) and MiniCircle with co-transfection agent MusFX (MC, MusFX). FIGS. 7-10 are graphical depictions charting corresponding differences between gene expression levels of plasmid and MiniCircle in the presence and absence of transfection co-factor Mus.FX at 13 weeks. Similar to FIG. 3 in the previous illustrative example, FIG. 7 clearly illustrates gene expression levels from transfection of MiniCircle alone resulting in a clear superiority over transfecting the same gene group utilizing a plasmid vector.

Gene expression differences between plasmid and MiniCircle transfection are attributable to the plasmid backbone silencing effect. The phenomenon is about the same as what was seen in earlier liver studies, however, the plasmid backbone DNA silencing effect in muscle is novel and of first impression. The plasmid backbone DNA silencing effect is illustrated in both embodiments, where luciferase levels in the mice receiving plasmid DNA is similar to that of MiniCircle group initially, but drops about one log shortly after DNA delivery while almost unchanged in MC group for more than 10 weeks, regardless of age and transfection co-factor such as MusFX.

Example 3

In a third illustrative embodiment, MiniCircle efficacy is enhanced by rational engineering of DNA sequences to improve functionality encoded by the MiniCircle DNA sequence. MiniCircle DNA can be used to express traditional bi-specific antibodies (bsAbs) with two scFv. In the illustrative third embodiment, either one or both scFvs are replaced by other elements to bind either target cells or effector T cells, such as natural ligands or synthesized peptides capable of binding receptors; furthermore, the scFv are alternatively replaced by Camel antibody elements, which have a smallest size. In this dual-target application the name of BTEC (bridge between target and effector cells) is used to represent all the formats. BTEC (the Bridge between Target and Effector Cells) is an engineered protein comprising two arms or parts: one arm recognizing target cells, the other arm recognizing effector cells via binding to the molecules on T (or NK) cell receptor signaling pathway. The BTEC can redirect the effector cells to the target cells and consequently lead to specific T (or NK) cells cytotoxicity on target cells. As listed in Table 1, NK: natural killer; TCR: T cell receptor; NCR: NK cell receptor; scTCR: recombinant single chain TCR; scFv: single chain variable fragment antibody; VHH: variable domains of camelid heavy chain-only antibody. CD3, CD28, 4-1BB, OX40 and TCR are involved in the TCR signaling pathway; CD16, CD56, NKG2D and NCR are involved in the NCR signaling pathway.

TABLE 1

|  | Target Cell | | Effector Cell | |
| --- | --- | --- | --- | --- |
|  | Tumor Cell | Infected Cell | T Cell | NK Cell |
| Molecular targets | Tumor specific antigens (TSA), Tumor associated antigens (TAA) | Viral antigens | CD3, CD28, 4-1BB, OX40, TCR | CD16, CD56, NKG2D, NCR |
| The part of BTEC molecule format | scTCR, scFv, V$_H$H, Ligand, Polypeptide | | | scFv, V$_H$H |

Figure 11:
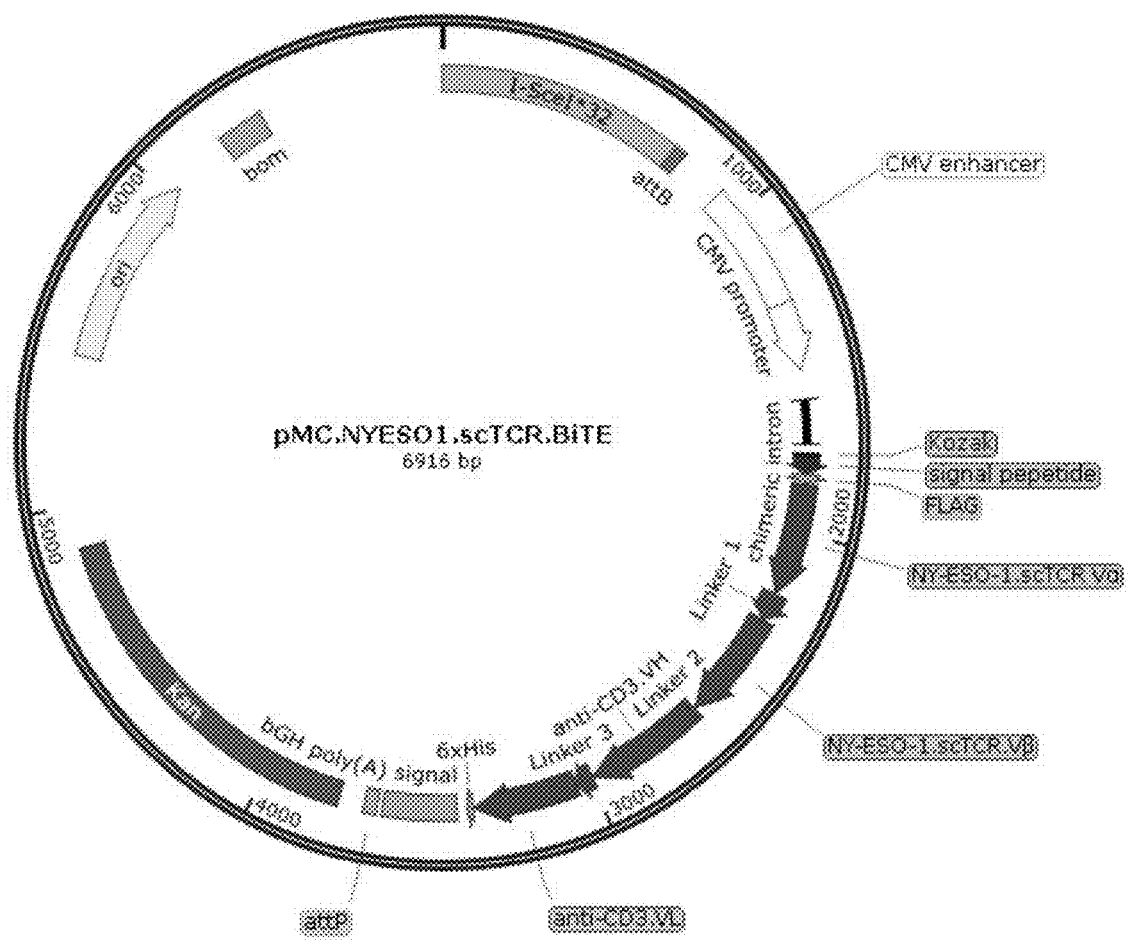
FIG. 11 is a schematic illustration of DNA MiniCircle vector NYES01.scTCR.BiTE.
Figure 12:
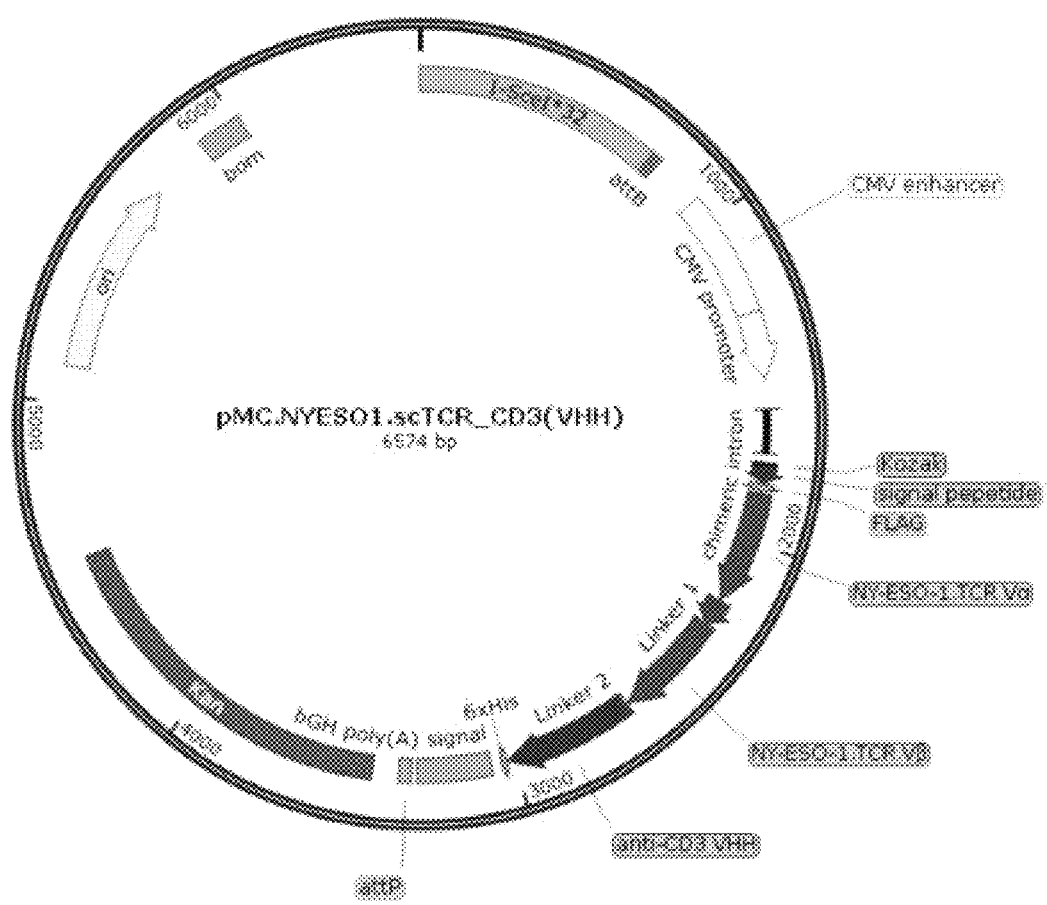
FIG. 12 is a schematic illustration of DNA MiniCircle vector NYES01.scTCR_CD3(VHH).
Figure 13:
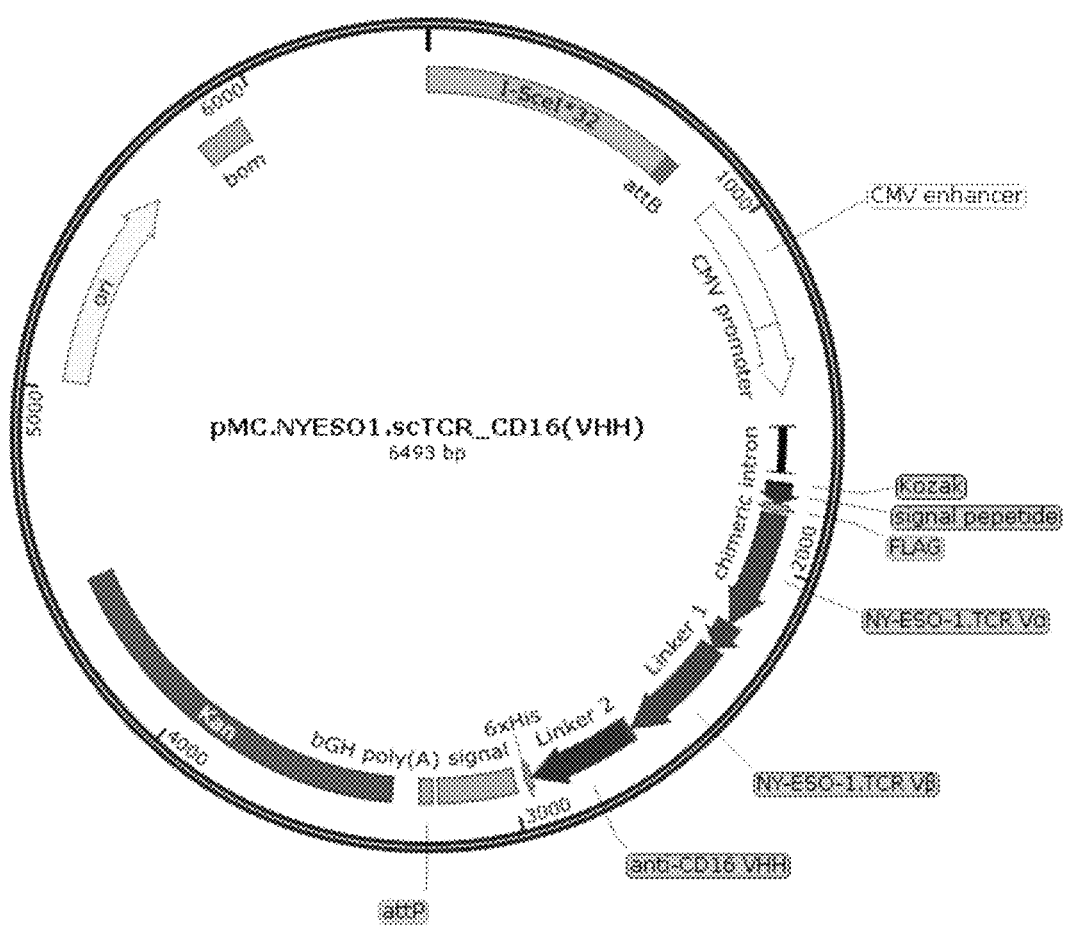
FIG. 13 is a schematic illustration of DNA MiniCircle vector NYES01.scTCR_CD16(VHH).
Figure 14:
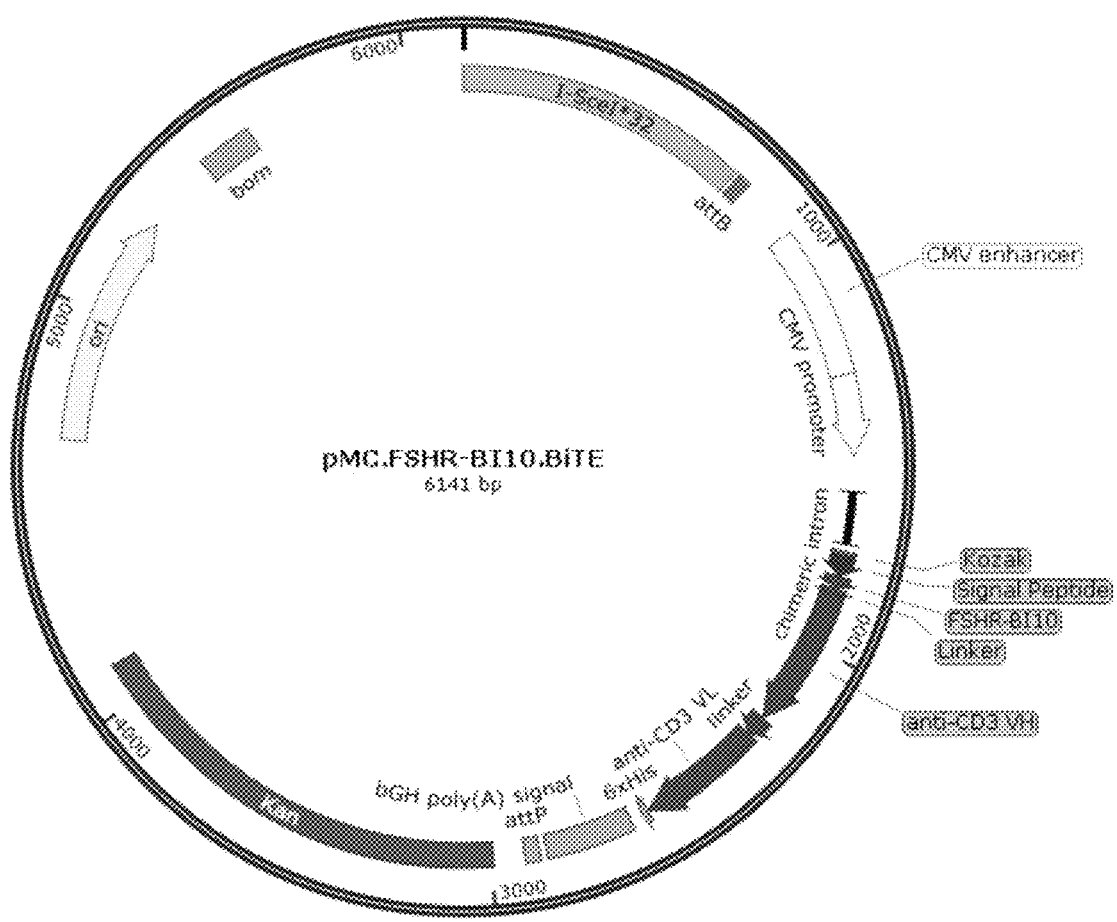
FIG. 14 is a schematic illustration of DNA MiniCircle vector FSHR/Bi10.BiTE.
Figure 15:
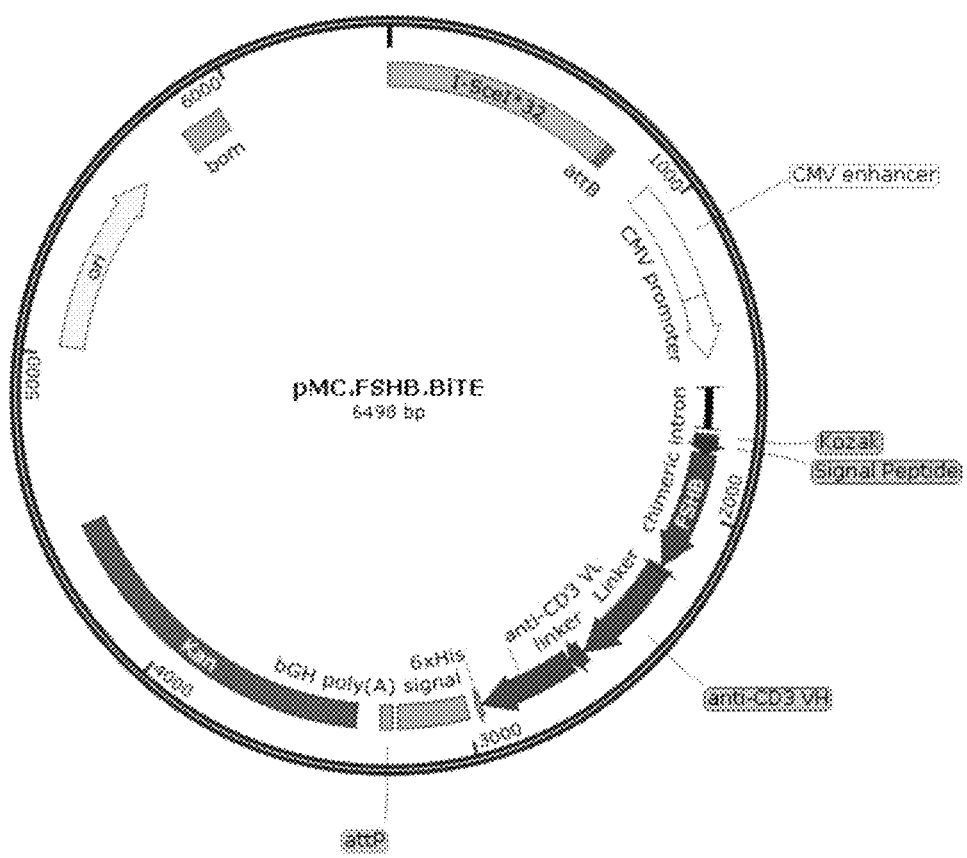
FIG. 15 is a schematic illustration of DNA MiniCircle vector FSHB/BiTE.
Figure 16:
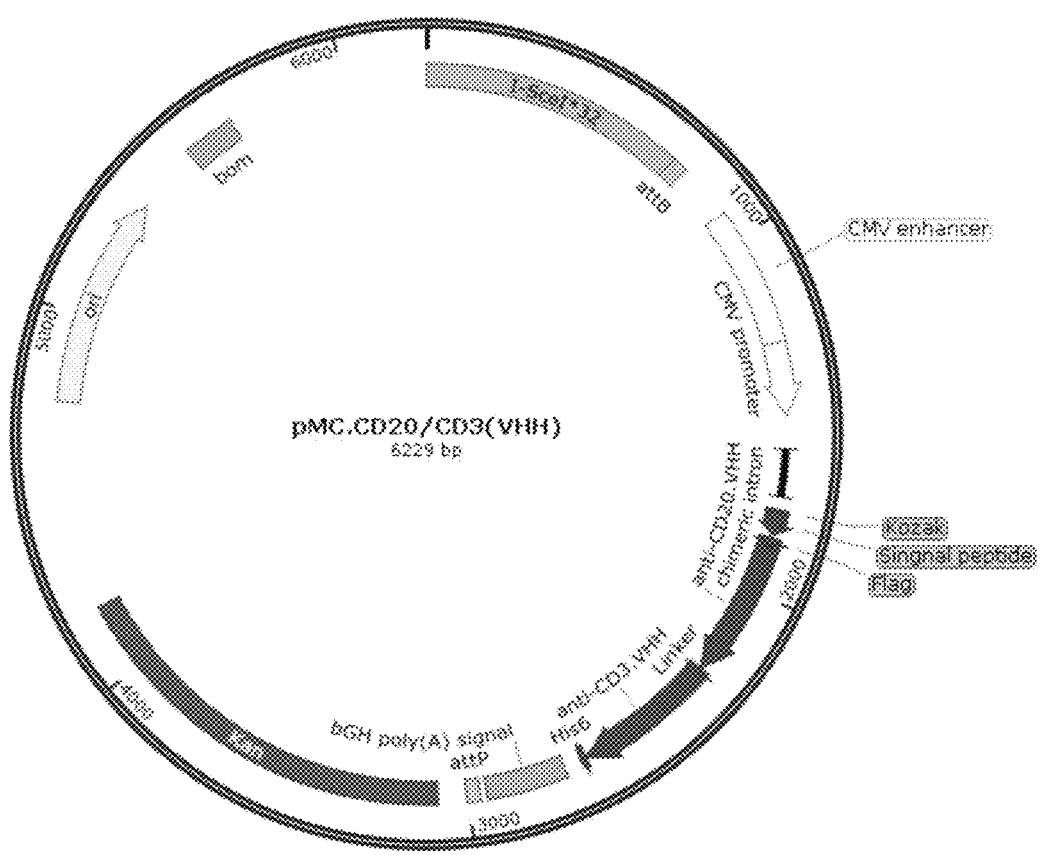
FIG. 16 is a schematic illustration of DNA MiniCircle vector CD20/CD3(VHH).
Figure 17:
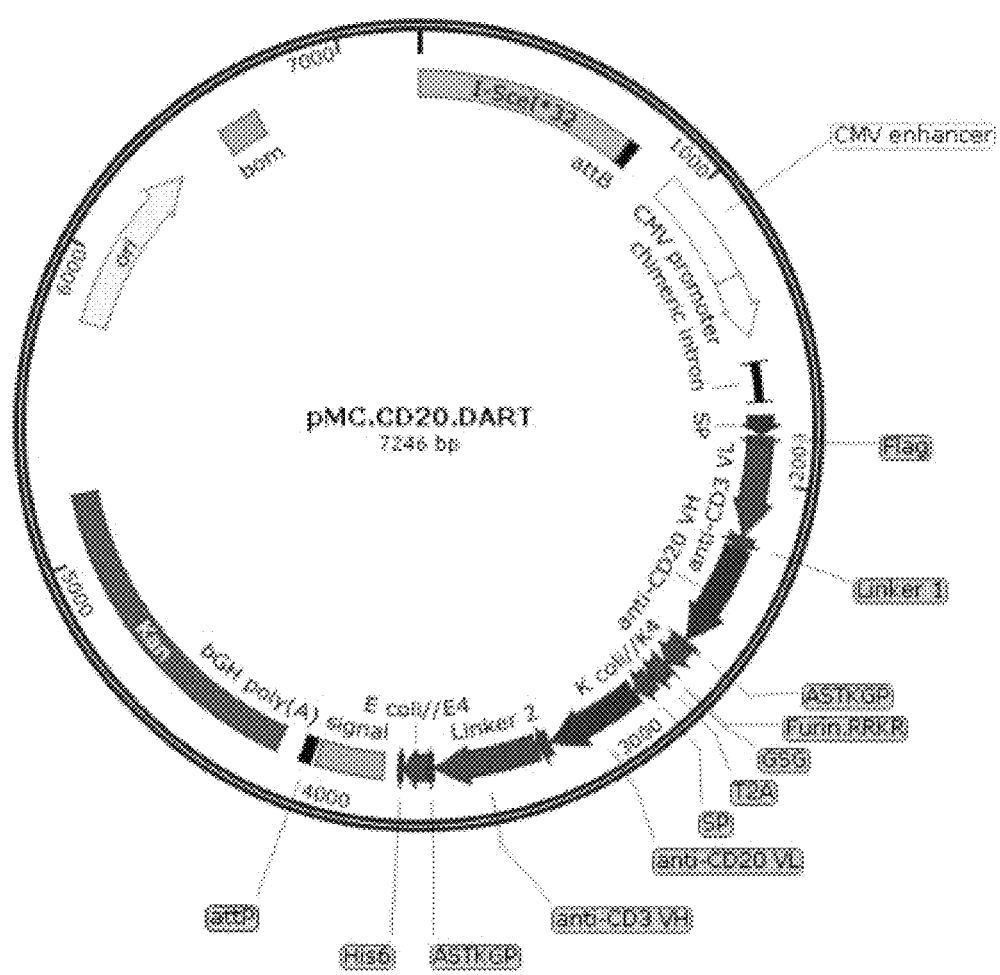
FIG. 17 is a schematic illustration of DNA MiniCircle vector CD20.DART.

Specific illustrative examples of Bridge between Target and Effector Cells are encoded by MiniCircle DNA including FIG. 11 DNA MiniCircle vector NYES01.scTCR.BiTE, FIG. 12 NYES01.scTCR_CD3(VHH), FIG. 13 MiniCircle vector NYES01.scTCR_CD16(VHH), FIG. 14 MiniCircle vector FSHR/Bi10.BiTE, FIG. 15 MiniCircle vector FSHB/BiTE, FIG. 16 DNA MiniCircle vector CD20/CD3(VHH) and FIG. 17 DNA MiniCircle vector CD20.DART. The illustrative examples demonstrate the improved BTEC applicability beyond T cells and target cell surface antigens. The figures illustrate in detail the general organization of Part A region with target cell specific binding portions and Part B region with specific effector cell binding portion.

In one embodiment, the portion of BTEC single-chain T-cell receptor is selected from (ScTCR), a single chain antibody (scFv), single domain antibodies (VHH), ligand (Ligand), polypeptide (Polypeptide) and others; the portion B is selected from a single chain antibody (scFv), single domain antibodies (VHH), Single-chain T-cell receptor (the scTCR), and others. In one embodiment, the portion B specific binding targets selected from: CD3, CD28, 4-1BB, OX40, TCR, CD16, CD56, NKG2D, NCR, and others. Preferably, the target cells include cancer cells, infected cells and other diseased cells; the effector cell is selected from T cells, NK cells and others. As an illustrative example, the ligand is derived from follicle stimulating hormone.

Example 4

In a direct and intended improvement of the claimed invention, the DNA MiniCircle encoding the BTEC (the Bridge between Target and Effector Cells) creates an engineered protein comprising two arms or parts: one arm recognizing target cells, the other arm recognizing effector cells via binding to the molecules on T (or NK) cell receptor signaling pathway as a direct result of an automated process. In the illustrative automated example, the target cells of a patient are captured and genetically sequenced. The corresponding DNA MiniCircle encoding for the BTEC is automatically generated based upon the genetic sequence of the captured disease cells to redirect the patient's effector cells to the target cells and consequently lead to specific T (or NK) cells cytotoxicity on target cells. Sequencing data from patient specific Tumor specific antigens (TSA), Tumor associated antigens (TAA) and Viral antigens are cross-referenced with T Cell (CD3, CD28, 4-1BB, OX40, TCR) and NK Cell (CD16, CD56, NKG2D, NCR) molecular targets. The DNA MiniCircle encoding for the BTEC is uniquely created based upon the patient's specific disease or tumor cell characteristics to encode for a disease cell target matched scTCR, scFv, VHH, Ligand, or Polypeptide region and optimal effector cell region matched scFv or VHH region.

In the description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

INDUSTRIAL APPLICABILITY

The claimed invention has industrial applicability in the biomedical arts. In particular, the claimed invention is directly relevant to the therapeutic administration of gene groups for mitigation and therapeutic effects against chronic diseases such as cancer.

SEQUENCE LISTING FREE TEXT

The instant application contains a Sequence Listing which has been submitted in ASCII format and is hereby incorporated by reference in its entirety. Said ASCII copy, created on Jun. 13, 2017, is named MC1_ST25.txt and is 46 kbytes in size.

CITATION LIST

Patent Literature

While a general understanding of DNA MiniCircle cultivation and production is taught by U.S. Pat. No. 9,233,174 to Chen et al., the claimed invention is distinguishable in its particular therapeutic applications. Related U.S. Pat. No. 8,445,454 is also distinguishable owing to the transfection improvements obtained through the claimed transfection co-factors as well as isolated MiniCircle transfection technique as applied to the benefits of using skeletal muscle over cardiac muscle as a transfection target.

<center>Non Patent Literature</center>

While transgene products expressed by intramuscular injection of plasmids was first reported in 1990 (Wolff J A et al., Science 247:1465, 1990), constant efforts to turn muscle into a factory of therapeutic gene products have met with limited success (Losordo D W et al., Am Heart J. 138:S132, 1999) and not effective from a therapeutic or cost perspective. Utilizing muscle cells as an uptake for MiniCircle delivery has been taught away from in the art as related literature focusing on liver delivery for MiniCircles are able to express trangene product more robustly than in muscle cells when compared to regular plasmid (Lijkwan M A (Wu J group), et al., Hum Gene Ther., 25:41, 2014; Chabot S et al., Gene Ther., 20:62, 2013). While liver studies of plasmid and MiniCircle (Chen Z Y et al., Mol Ther 2003, 2008) have noted plasmid backbone DNA silencing, the instant application is of first impression with respect to DNA backbone silencing in muscle tissue.

---

Sequence Listing

SEQ ID NO: 1
AntiCD20VHH
PVQLVESGGGLVQAGDSLRLSCAASGRTFGIGTMGWFRQPPGKEREFVAA
IRWSTGGTRYADSVKGRFTISRDNAKLTVDLQMDSLKPEDTAVYYCAADR
LSLDLSGRYHYNPAVYDYWGQGTQVTVSS SEQ ID NO: 2
AntiCD20VHHGene
CCGGTGCAGCTGGTGGAGTCTGGGGGAGGCTTGGT
GCAGGCTGGGGATTCTCTGAGACTCTCCTGTGCTGC
CTCTGGACGCACCTTCGGTATTGGTACCATGGGCTGG
TTCCGCCAACCTCCAGGGAAGGAGCGTGAATTTGTAG
CAGCTATTAGGTGGAGTACTGGTGGCACTCGCTATGC
AGACTCCGTGAAGGGCCGATTCACCATCTCCCGAGAC
AACGCCAAGCTCACGGTAGACCTGCAAATGGACAGCC
TGAAACCTGAAGACACGGCCGTTTATTACTGTGCAGC
AGATAGACTGTCCCTTGATTTAAGTGGTCGTTACCACT
ACAACCCCGCCGTGTATGACTATTGGGGCCAGGGGA
CCCAGGTCACCGTCTCCTCA SEQ ID NO: 3
Anti-CD20 VL
DIVMTQTPLSLPVTPGEPASISCRSSKSLLHSNGITYLYW
YLQKPGQSPQLLIYQMSNLVSGVPDRFSGSGSGTDFTL
KISRVEAEDVGVYYCAQNLELPYTFGGGTKVEIK SEQ ID NO: 4
Anti-CD20VHAA
LVQSGAEVKKPGSSVKVSCKASGYAFSYSWINWV
RQAPGQGLEWMGRIFPGDGDTDYNGKFKGRVTITADKS
TSTAYMELSSLRSEDTAVYYCARNVFDGYWLVYWGQGT
LVTVSS SEQ ID NO: 5
Follicle-stimulating hormone (FSH) amino Acid
sequence
MKTLQFFFLFCCWKAICCNSCELTNITIAIEKEECRFCISI
NTTWCAGYCYTRDLVYKDPARPKIQKTCTFKELVYETVR
VPGCAHHADSLYTYPVATQCHCGKCDSDSTDCTVRGLG
PSYCSFGEMKE SEQ ID NO: 6
Follicle-stimulating hormone
Receptor binding inhibition
10 peptide fragments
(FSHR-BI10) amino acid sequence
TENLEPNGEG SEQ ID NO: 7
NY-ESO-1.TCR Vα
QEVTQIPAALSVPEGENLVLNCSFTDSAIYNLQWFRQDP
GKGLTSLLLIQSSQREQTSGRLNASLDKSSGRSTLYIAAS
QPGDSATYLCAVRPTSGGSYIPTFGRGTSLIVHPYP SEQ ID NO: 8
NY-ESO-1.TCR Vβ
PGVTQTPKFQVLKTGQSMTLQCAQDMNHEYMSWYRQ
DPGMGLRLIHYSVGAGITDQGEVPNGYNVSRSTTEDFP
LRLLSAAPSQTSVYFCASSYVGNTGELFFGEGSRLTVL SEQ ID NO: 9
AntiCD3VHH
QVQLQESGGGLVQAGGSLRLSCAASGRTFSNYHMGWF
RQAPGKERELVAAISGSGGSTYYTDSVKGRFTISRNNAK
NTMSLQMSNLKPEDTGVYYCTTPTEKGSSIDYWGQGT
QVTVSSGRYPYDVPDY SEQ ID NO: 10
AntiCD3VHHGene
CAAGTCCAACTTCAGGAATCCGGGGGTGGGCTGGTC
CAGGCAGGCGGGTCCCTCCGCCTTAGCTGCGCAGCA
TCCGGGCGCACGTTTAGTAACTATCACATGGGATGGTT
CCGCCAGGCACCCGGTAAAGAGCGGGAATTGGTAGC
CGCCATAAGCGGTAGTGGAGGTTCAACCTATTATACCG
ACAGTGTAAAGGGGCGATTTACAATTTCACGGAATAAC
GCAAAGAACACAATGTCACTTCAAATGTCAAACCTCAA
ACCTGAAGACACGGGTGTGTATTATTGTACCACCCCCA
CGGAAAAAGGGTCATCTATCGACTATTGGGGCCAAGG
AACGCAAGTAACAGTTAGCTCTGGTCGATACCCCTATG
ACGTTCCTGACTAC SEQ ID NO: 11
AntiCD16VHH
EVQLVESGGGLVQPGGSLTLSCVAAGSIFTFAMSWYRQ
APRKERELVARIGTDDETMYKDSVKGRFTISRDNVKRTA
GLQMNNLKPEDTAVYYCNARTDYRD SEQ ID NO: 12
AntiCD3VL
DIVLTQSPATLSLSPGERATLSCRASQSVSYMNWYQQK
PGKAPKRWIYDTSKVASGVPARFSGSGSGTDYSLTINSL
EAEDAATYYCQQWSSNPLTFGGGTKVEIK SEQ ID NO: 13
AntiCD3VH
DVQLVQSGAEVKKPGASVKVSCKASGYTFTRYTMHWV
RQAPGQGLEWIGYINPSRGYTNYADSVKGRFTITTDKST
STAYMELSSLRSEDTATYYCARYYDDHYCLDYWGQGTT
VTVSS SEQ ID NO: 14
AntiCD20-DART/BsAbChain1
DIVLTQSPATLSLSPGERATLSCRASQSVSYMNWYQQK
PGKAPKRWIYDTSKVASGVPARFSGSGSGTDYSLTINSL
EAEDAATYYCQQWSSNPLTFGGGTKVEIKGGGGSGGG
GSGGGGSQVQLVQSGAEVKKPGSSVKVSCKASGYAFS
YSWINWVRQAPGQGLEWMGRIFPGDGDTDYNGKFKG
RVTITADKSTSTAYMELSSLRSEDTAVYYCARNVFDGYW
LVYWGQGTLVTVSSASTKGPKVSALKEKVSALKEKVSAL
KEKVSALKE SEQ ID NO: 15
AntiCD20-DART/BsAbChain2
DIVMTQTPLSLPVTPGEPASISCRSSKSLLHSNGITYLYW
YLQKPGQSPQLLIYQMSNLVSGVPDRFSGSGSGTDFTL
KISRVEAEDVGVYYCAQNLELPYTFGGGTKVEIKGGGG
SGGGGSGGGGSDVQLVQSGAEVKKPGASVKVSCKAS
GYTFTRYTMHWVRQAPGQGLEWIGYINPSRGYTNYADS
VKGRFTITTDKSTSTAYMELSSLRSEDTATYYCARYYDD
HYCLDYWGQGTTVTVSSASTKGPEVSALEKEVSALEKE
VSALEKEVSALEK Sequence Listing SEQ ID NO: 16
AntiCD20VHH/AntiCD3VHHGene
```
AAGCTTgccaccatggccATGTGGTGGCGCCTGTGGTGGC
TGCTGCTGCTGCTGCTGCTGCTGTGGCCCATGGTGT
GGGCCgccgccgactacaaagatgatgacgataagCCGGTGCAG
CTGGTGGAGTCTGGGGGAGGCTTGGTGCAGGCTGG
GGATTCTCTGAGACTCTCCTGTGCTGCCTCTGGACGC
ACCTTCGGTATTGGTACCATGGGCTGGTTCCGCCAAC
CTCCAGGGAAGGAGCGTGAATTTGTAGCAGCTATTAG
GTGGAGTACTGGTGGCACTCGCTATGCAGACTCCGTG
AAGGGCCGATTCACCATCTCCCGAGACAACGCCAAGC
TCACGGTAGACCTGCAAATGGACAGCCTGAAACCTGA
AGACACGGCCGTTTATTACTGTGCAGCAGATAGACTGT
CCCTTGATTTAAGTGGTCGTTACCACTACAACCCCGCC
GTGTATGACTATTGGGGCCAGGGGACCCAGGTCACC
GTCTCCTCAggaggtggtggctccCAAGTCCAACTTCAGGAA
TCCGGGGGTGGGCTGGTCCAGGCAGGCGGGTCCCT
CCGCCTTAGCTGCGCAGCATCCGGGCGCACGTTTAGT
AACTATCACATGGGATGGTTCCGCCAGGCACCCGGTA
AAGAGCGGGAATTGGTAGCCGCCATAAGCGGTAGTGG
AGGTTCAACCTATTATACCGACAGTGTAAAGGGGCGAT
TTACAATTTCACGGAATAACGCAAAGAACACAATGTCA
CTTCAAATGTCAAACCTCAAACCTGAAGACACGGGTG
TGTATTATTGTACCACCCCCACGGAAAAAGGGTCATCT
ATCGACTATTGGGGCCAAGGAACGCAAGTAACAGTTA
GCTCTGGTCGATACCCCTATGACGTTCCTGACTACcatc
atcaccatcatcattagAGATCT
```

SEQ ID NO: 17
AntiCD20DARTGene
```
AAGCTTgccaccatggccATGTGGTGGCGCCTGTGGTGGC
TGCTGCTGCTGCTGCTGCTGTGGCCCATGGTGT
GGGCCgccgccgactacaaagatgatgacgataaggacattgtactgacc
cagtctccagcaactctgtctctgtctccaggggagcgtgccaccctgag
ctgcagagccagtcaaagtgtaagttacatgaactggtaccagcagaagc
cgggcaaggcacccaaaagatggatttatgacacatccaaagtggcttct
ggagtccctgctcgcttcagtggcagtgggtctgggaccgactactctct
cacaatcaacagcttggaggctgaagatgctgccacttattactgccaac
agtggagtagtaacccgctcacgttcggtggcgggaccaaggtggagatc
aaaGGTGGTGGTGGTTCTGGCGGCGGCGGCTCCGGTGGTGGTGGTTCTca
ggtgcaattggtgcagtctggcgctgaagttaagaagcctggggagttcag
tgaaggtctcctgcaaggcttcaggatacgccttcagctattcttggatc
aattgggtgcggcaggcgcctggacaagggctcgagtggatgggacggat
ctttcccggcgatggggatactgactacaatgggaaattcaagggcagag
tcacaattaccgccgacaaatccactagcacagcctatatggagctgagc
agcctgagatccgaggacacggccgtgtattactgtgcaagaaatgtatt
gatggttactggttgttttactggggccaggggaaccctggtcaccgtctc
ctccGCCAGCACAAAGGGACCTAAGGTGTCAGCTCTCAAGGAGAAGGTCT
CTGCTCTTAAAGAAAAGTCTCAGCACTGAAAGAGAAGGTTTCT
GCATTGAAGGAGcggagaaagagaggcagcggcgagggaagag
gatctctgctgacatgcggcgacgtggaagagaatccaggacctATGTGG
TGGCGCCTGTGGTGGCTGCTGCTGCTGCTGCTG
CTGTGGCCCATGGTGTGGGCCgccgccgatatcgtgatgaccc
agactccactctccctgcccgtcacccctggagagcccgccagcattagc
tgcaggtctagcaagagcctcttgcacagcaatggcatcactttatttgta
ttggtacctgcaaaagccaggccagtctcccacagctcctgatttatcaaa
tgtccaaccttgtctctggcgtccctgaccggttctcaggatccgggtca
ggcactgatttcacactgaaaatcagcagggtggaggctgaggatgttgg
agtttattactgcgctcagaatctagaacttccttacaccttcggcggag
ggaccaaggtggagatcaaaGGTGGTGGTGGTTCTGGCGGCGGCGGCTCC
GGTGGTGGTGGTTCTGgacgtccaactggtgcagtcagggcctgaagtgaa
aaaacctggggcctcagtgaaggtgtcctgcaaggcttctggctacacct
ttactaggtacacgatgcactgggtaaggcaggcacctggacagggtctg
gaatggattggatacattaatcctagccgtggttatactaattacgcaga
cagcgtcaagggccgcttcacaatcactacagacaaatccaccagcacag
cctacatggaactgagcagcctgcgttctgagggacactgcaacctattac
tgtgcaagatattatgatgatcattactgccttgactactggggccaagg
caccacggtcaccgtctcctcaGCCAGCACAAAGGGACCTGAGGTTAGTG
CATTGGAGAAAGAAGTAAGCGCATTGGAAAAGAAGTGTCTGCATTGGAG
AAAGAGGTCTCCGCGCTCGAAAAGcatcatcaccatcatcatTAAagatc
t
```

I claim:

1. A method for treatment of disease in a patient, the method comprising:
preparing a bispecific antibody MiniCircle DNA vector for therapeutic delivery, wherein bacterial backbone plasmid sequences are absent from the vector, by combining the bispecific antibody MiniCircle DNA vector with a co-transfection aid selected from the group consisting of glycyrrhizin (GL), and Ginseng Rh1 (GS); and administering by local delivery to skeletal muscle in said patient an effective dose of said bispecific antibody MiniCircle DNA vector for treatment of disease in said patient.

2. The method of claim 1, wherein said bispecific antibody Minicircle DNA vector encodes a bispecific antibody that targets a tumor specific antigen.

3. The method of claim 1, wherein said bispecific antibody Minicircle DNA vector encodes a bispecific antibody that targets a tumor associated antigen.

* * * * *

SEQUENCE LISTING

<160> NUMBER OF SEQ ID NOS: 17

<210> SEQ ID NO 1
<211> LENGTH: 129
<212> TYPE: PRT
<213> ORGANISM: Artificial Sequence
<220> FEATURE:
<223> OTHER INFORMATION: Artificial Sequence created by rational design

<400> SEQUENCE: 1

```
Pro Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Gly Ile Gly
            20                  25                  30

Thr Met Gly Trp Phe Arg Gln Pro Pro Gly Lys Glu Arg Glu Phe Val
        35                  40                  45

Ala Ala Ile Arg Trp Ser Thr Gly Gly Thr Arg Tyr Ala Asp Ser Val
    50                  55                  60

Lys Gly Arg Phe Thr Ile Ser Arg Asp Asn Ala Lys Leu Thr Val Asp
65                  70                  75                  80

Leu Gln Met Asp Ser Leu Lys Pro Glu Asp Thr Ala Val Tyr Tyr Cys
                85                  90                  95

Ala Ala Asp Arg Leu Ser Leu Asp Leu Ser Gly Arg Tyr His Tyr Asn
            100                 105                 110

Pro Ala Val Tyr Asp Tyr Trp Gly Gln Gly Thr Gln Val Thr Val Ser
        115                 120                 125
```

Ser

<210> SEQ ID NO 2
<211> LENGTH: 387
<212> TYPE: DNA
<213> ORGANISM: Artificial Sequence
<220> FEATURE:
<223> OTHER INFORMATION: Artificial Sequence constructed by rational
      design

<400> SEQUENCE: 2

```
ccggtgcagc tggtggagtc tgggggaggc ttggtgcagg ctggggattc tctgagactc      60
tcctgtgctg cctctggacg caccttcggt attggtacca tgggctggtt ccgccaacct     120
ccagggaagg agcgtgaatt tgtagcagct attaggtgga gtactggtgg cactcgctat     180
gcagactccg tgaagggccg attcaccatc tcccgagaca acgccaagct cacggtagac     240
ctgcaaatgg acagcctgaa acctgaagac acggccgttt attactgtgc agcagataga     300
ctgtcccttg atttaagtgg tcgttaccac tacaaccccg ccgtgtatga ctattggggc     360
caggggaccc aggtcaccgt ctcctca                                         387
```

<210> SEQ ID NO 3
<211> LENGTH: 112
<212> TYPE: PRT
<213> ORGANISM: Artificial Sequence
<220> FEATURE:
<223> OTHER INFORMATION: Artificial Sequence constructed by rational
      design

<400> SEQUENCE: 3

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 4
<211> LENGTH: 116
<212> TYPE: PRT
<213> ORGANISM: Artificial Sequence
<220> FEATURE:
<223> OTHER INFORMATION: Artificial Sequence constructed by rational
      design

<400> SEQUENCE: 4

```
Leu Val Gln Ser Gly Ala Glu Val Lys Lys Pro Gly Ser Ser Val Lys
1               5                   10                  15

Val Ser Cys Lys Ala Ser Gly Tyr Ala Phe Ser Tyr Ser Trp Ile Asn
            20                  25                  30

Trp Val Arg Gln Ala Pro Gly Gln Gly Leu Glu Trp Met Gly Arg Ile
        35                  40                  45
```

-continued

Phe Pro Gly Asp Gly Asp Thr Asp Tyr Asn Gly Lys Phe Lys Gly Arg
         50                  55                  60

Val Thr Ile Thr Ala Asp Lys Ser Thr Ser Thr Ala Tyr Met Glu Leu
 65                  70                  75                  80

Ser Ser Leu Arg Ser Glu Asp Thr Ala Val Tyr Tyr Cys Ala Arg Asn
                 85                  90                  95

Val Phe Asp Gly Tyr Trp Leu Val Tyr Trp Gly Gln Gly Thr Leu Val
            100                 105                 110

Thr Val Ser Ser
            115

<210> SEQ ID NO 5
<211> LENGTH: 129
<212> TYPE: PRT
<213> ORGANISM: Artificial Sequence
<220> FEATURE:
<223> OTHER INFORMATION: Artificial Sequence constructed by rational
      design

<400> SEQUENCE: 5

Met Lys Thr Leu Gln Phe Phe Leu Phe Cys Cys Trp Lys Ala Ile
 1               5                  10                  15

Cys Cys Asn Ser Cys Glu Leu Thr Asn Ile Thr Ile Ala Ile Glu Lys
                 20                  25                  30

Glu Glu Cys Arg Phe Cys Ile Ser Ile Asn Thr Thr Trp Cys Ala Gly
             35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
             85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu

<210> SEQ ID NO 6
<211> LENGTH: 10
<212> TYPE: PRT
<213> ORGANISM: Artificial Sequence
<220> FEATURE:
<223> OTHER INFORMATION: Artificial Sequence constructed by rational
      design

<400> SEQUENCE: 6

Thr Glu Asn Leu Glu Pro Asn Gly Glu Gly
 1               5                  10

<210> SEQ ID NO 7
<211> LENGTH: 115
<212> TYPE: PRT
<213> ORGANISM: Artificial Sequence
<220> FEATURE:
<223> OTHER INFORMATION: Artificial Sequence constructed by rational
      design

<400> SEQUENCE: 7

Gln Glu Val Thr Gln Ile Pro Ala Ala Leu Ser Val Pro Glu Gly Glu

```
                1               5                   10                  15
            Asn Leu Val Leu Asn Cys Ser Phe Thr Asp Ser Ala Ile Tyr Asn Leu
                            20                  25                  30

Gln Trp Phe Arg Gln Asp Pro Gly Lys Gly Leu Thr Ser Leu Leu Leu
                            35                  40                  45

Ile Gln Ser Ser Gln Arg Glu Gln Thr Ser Gly Arg Leu Asn Ala Ser
             50                  55                  60

Leu Asp Lys Ser Ser Gly Arg Ser Thr Leu Tyr Ile Ala Ala Ser Gln
             65                  70                  75                  80

Pro Gly Asp Ser Ala Thr Tyr Leu Cys Ala Val Arg Pro Thr Ser Gly
                            85                  90                  95

Gly Ser Tyr Ile Pro Thr Phe Gly Arg Gly Thr Ser Leu Ile Val His
                            100                 105                 110

Pro Tyr Pro
                        115
```

<210> SEQ ID NO 8
<211> LENGTH: 112
<212> TYPE: PRT
<213> ORGANISM: Artificial Sequence
<220> FEATURE:
<223> OTHER INFORMATION: All sequence listings are Artificial Sequence
      constructed by rational design

<400> SEQUENCE: 8

```
            Pro Gly Val Thr Gln Thr Pro Lys Phe Gln Val Leu Lys Thr Gly Gln
             1               5                   10                  15

Ser Met Thr Leu Gln Cys Ala Gln Asp Met Asn His Glu Tyr Met Ser
                            20                  25                  30

Trp Tyr Arg Gln Asp Pro Gly Met Gly Leu Arg Leu Ile His Tyr Ser
                            35                  40                  45

Val Gly Ala Gly Ile Thr Asp Gln Gly Glu Val Pro Asn Gly Tyr Asn
             50                  55                  60

Val Ser Arg Ser Thr Thr Glu Asp Phe Pro Leu Arg Leu Leu Ser Ala
             65                  70                  75                  80

Ala Pro Ser Gln Thr Ser Val Tyr Phe Cys Ala Ser Ser Tyr Val Gly
                            85                  90                  95

Asn Thr Gly Glu Leu Phe Phe Gly Glu Gly Ser Arg Leu Thr Val Leu
                            100                 105                 110
```

<210> SEQ ID NO 9
<211> LENGTH: 129
<212> TYPE: PRT
<213> ORGANISM: Artificial Sequence
<220> FEATURE:
<223> OTHER INFORMATION: All sequence listings are Artificial Sequence
      constructed by rational design

<400> SEQUENCE: 9

```
            Gln Val Gln Leu Gln Glu Ser Gly Gly Gly Leu Val Gln Ala Gly Gly
             1               5                   10                  15

Ser Leu Arg Leu Ser Cys Ala Ala Ser Gly Arg Thr Phe Ser Asn Tyr
                            20                  25                  30

His Met Gly Trp Phe Arg Gln Ala Pro Gly Lys Glu Arg Glu Leu Val
                            35                  40                  45

Ala Ala Ile Ser Gly Ser Gly Gly Ser Thr Tyr Tyr Thr Asp Ser Val
             50                  55                  60

Lys Gly Arg Phe Thr Ile Ser Arg Asn Asn Ala Lys Asn Thr Met Ser
```

```
            65                  70                  75                  80
Leu Gln Met Ser Asn Leu Lys Pro Glu Asp Thr Gly Val Tyr Tyr Cys
                    85                  90                  95

Thr Thr Pro Thr Glu Lys Gly Ser Ser Ile Asp Tyr Trp Gly Gln Gly
            100                 105                 110

Thr Gln Val Thr Val Ser Ser Gly Arg Tyr Pro Tyr Asp Val Pro Asp
            115                 120                 125

Tyr

<210> SEQ ID NO 10
<211> LENGTH: 387
<212> TYPE: PRT
<213> ORGANISM: Artificial Sequence
<220> FEATURE:
<223> OTHER INFORMATION: Artificial Sequence constructed by rational
      design

<400> SEQUENCE: 10

Cys Ala Ala Gly Thr Cys Cys Ala Ala Cys Thr Thr Cys Ala Gly Gly
1               5                   10                  15

Ala Ala Thr Cys Cys Gly Gly Gly Gly Thr Gly Gly Gly Cys Thr
            20                  25                  30

Gly Gly Thr Cys Cys Ala Gly Gly Cys Ala Gly Gly Cys Gly Gly Gly
            35                  40                  45

Thr Cys Cys Thr Cys Cys Gly Cys Cys Thr Thr Ala Gly Cys Thr
            50                  55                  60

Gly Cys Gly Cys Ala Gly Cys Ala Thr Cys Cys Gly Gly Cys Gly
65                  70                  75                  80

Cys Ala Cys Gly Thr Thr Thr Ala Gly Thr Ala Ala Cys Thr Ala Thr
                    85                  90                  95

Cys Ala Cys Ala Thr Gly Gly Ala Thr Gly Gly Thr Thr Cys Cys
                    100                 105                 110

Gly Cys Cys Ala Gly Gly Cys Ala Cys Cys Gly Gly Thr Ala Ala
                    115                 120                 125

Ala Gly Ala Gly Cys Gly Gly Ala Ala Thr Thr Gly Gly Thr Ala
                    130                 135                 140

Gly Cys Cys Gly Cys Cys Ala Thr Ala Ala Gly Cys Gly Gly Thr Ala
145                 150                 155                 160

Gly Thr Gly Gly Ala Gly Gly Thr Thr Cys Ala Ala Cys Cys Thr Ala
                    165                 170                 175

Thr Thr Ala Thr Ala Cys Cys Gly Ala Cys Ala Gly Thr Gly Thr Ala
                    180                 185                 190

Ala Ala Gly Gly Gly Cys Gly Ala Thr Thr Thr Ala Cys Cys Ala
                    195                 200                 205

Thr Thr Thr Cys Ala Cys Gly Gly Ala Thr Ala Ala Cys Gly Cys
                    210                 215                 220

Ala Ala Ala Gly Ala Ala Cys Ala Cys Ala Ala Thr Gly Thr Cys Ala
225                 230                 235                 240

Cys Thr Thr Cys Ala Ala Ala Thr Gly Thr Cys Ala Ala Cys Cys
                    245                 250                 255

Thr Cys Ala Ala Ala Cys Cys Thr Gly Ala Gly Ala Cys Ala Cys
                    260                 265                 270

Gly Gly Gly Thr Gly Thr Gly Thr Ala Thr Thr Ala Thr Gly Thr
                    275                 280                 285

Ala Cys Cys Ala Cys Cys Cys Cys Cys Ala Cys Gly Gly Ala Ala Ala
```

```
            290                 295                 300
Ala Ala Gly Gly Gly Thr Cys Ala Thr Cys Thr Ala Thr Cys Gly Ala
305                 310                 315                 320

Cys Thr Ala Thr Thr Gly Gly Gly Cys Cys Ala Ala Gly Gly Ala
                325                 330                 335

Ala Cys Gly Cys Ala Ala Gly Thr Ala Ala Cys Ala Gly Thr Thr Ala
                340                 345                 350

Gly Cys Thr Cys Thr Gly Gly Thr Cys Gly Ala Thr Ala Cys Cys Cys
            355                 360                 365

Cys Thr Ala Thr Gly Ala Cys Gly Thr Thr Cys Cys Thr Gly Ala Cys
            370                 375                 380

Thr Ala Cys
385
```

<210> SEQ ID NO 11
<211> LENGTH: 102
<212> TYPE: PRT
<213> ORGANISM: Artificial Sequence
<220> FEATURE:
<223> OTHER INFORMATION: Artificial Sequence constructed by rational
      design

<400> SEQUENCE: 11

```
Glu Val Gln Leu Val Glu Ser Gly Gly Gly Leu Val Gln Pro Gly Gly
1               5                   10                  15

Ser Leu Thr Leu Ser Cys Val Ala Ala Gly Ser Ile Phe Thr Phe Ala
            20                  25                  30

Met Ser Trp Tyr Arg Gln Ala Pro Arg Lys Glu Arg Gly Leu Val Ala
        35                  40                  45

Arg Ile Gly Thr Asp Asp Glu Thr Met Tyr Lys Asp Ser Val Lys Gly
    50                  55                  60

Arg Phe Thr Ile Ser Arg Asp Asn Val Lys Arg Thr Ala Gly Leu Gln
65                  70                  75                  80

Met Asn Asn Leu Lys Pro Glu Asp Thr Ala Val Tyr Tyr Cys Asn Ala
                85                  90                  95

Arg Thr Asp Tyr Arg Asp
            100
```

<210> SEQ ID NO 12
<211> LENGTH: 106
<212> TYPE: PRT
<213> ORGANISM: Artificial Sequence
<220> FEATURE:
<223> OTHER INFORMATION: Artificial Sequence constructed by rational
      design

<400> SEQUENCE: 12

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
```

```
                                85                   90                   95
Phe Gly Gly Gly Thr Lys Val Glu Ile Lys
                100                 105

<210> SEQ ID NO 13
<211> LENGTH: 119
<212> TYPE: PRT
<213> ORGANISM: Artificial Sequence
<220> FEATURE:
<223> OTHER INFORMATION: Artificial Sequence constructed by rational
      design

<400> SEQUENCE: 13

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
        50                  55                  60

Lys Gly Arg Phe Thr Ile Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
                100                 105                 110

Thr Thr Val Thr Val Ser Ser
            115

<210> SEQ ID NO 14
<211> LENGTH: 274
<212> TYPE: PRT
<213> ORGANISM: Artificial Sequence
<220> FEATURE:
<223> OTHER INFORMATION: Artificial Sequence constructed by rational
      design

<400> SEQUENCE: 14

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
                20                  25                  30

Asn Trp Tyr Gln Gln Lys Pro Gly Lys Ala Pro Lys Arg Trp Ile Tyr
            35                  40                  45

Asp Thr Ser Lys Val Ala Ser Gly Val Pro Ala Arg Phe Ser Gly Ser
        50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys Gly Gly Gly Gly Ser Gly
                100                 105                 110

Gly Gly Gly Ser Gly Gly Gly Gly Ser Gln Val Gln Leu Val Gln Ser
            115                 120                 125

Gly Ala Glu Val Lys Lys Pro Gly Ser Ser Val Lys Val Ser Cys Lys
        130                 135                 140

Ala Ser Gly Tyr Ala Phe Ser Tyr Ser Trp Ile Asn Trp Val Arg Gln
```

```
                145                 150                 155                 160
Ala Pro Gly Gln Gly Leu Glu Trp Met Gly Arg Ile Phe Pro Gly Asp
                    165                 170                 175

Gly Asp Thr Asp Tyr Asn Gly Lys Phe Lys Gly Arg Val Thr Ile Thr
                180                 185                 190

Ala Asp Lys Ser Thr Ser Thr Ala Tyr Met Glu Leu Ser Ser Leu Arg
            195                 200                 205

Ser Glu Asp Thr Ala Val Tyr Tyr Cys Ala Arg Asn Val Phe Asp Gly
        210                 215                 220

Tyr Trp Leu Val Tyr Trp Gly Gln Gly Thr Leu Val Thr Val Ser Ser
225                 230                 235                 240

Ala Ser Thr Lys Gly Pro Lys Val Ser Ala Leu Lys Glu Lys Val Ser
                245                 250                 255

Ala Leu Lys Glu Lys Val Ser Ala Leu Lys Glu Lys Val Ser Ala Leu
            260                 265                 270

Lys Glu

<210> SEQ ID NO 15
<211> LENGTH: 280
<212> TYPE: PRT
<213> ORGANISM: Artificial Sequence
<220> FEATURE:
<223> OTHER INFORMATION: Artificial Sequence constructed by rational
      design

<400> SEQUENCE: 15

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Gly Gly Gly Gly Ser Gly Gly Gly Ser Gly Gly Gly Gly Ser Asp
            115                 120                 125

Val Gln Leu Val Gln Ser Gly Ala Glu Val Lys Lys Pro Gly Ala Ser
        130                 135                 140

Val Lys Val Ser Cys Lys Ala Ser Gly Tyr Thr Phe Thr Arg Tyr Thr
145                 150                 155                 160

Met His Trp Val Arg Gln Ala Pro Gly Gln Gly Leu Glu Trp Ile Gly
                165                 170                 175

Tyr Ile Asn Pro Ser Arg Gly Tyr Thr Asn Tyr Ala Asp Ser Val Lys
            180                 185                 190

Gly Arg Phe Thr Ile Thr Thr Asp Lys Ser Thr Ser Thr Ala Tyr Met
        195                 200                 205

Glu Leu Ser Ser Leu Arg Ser Glu Asp Thr Ala Thr Tyr Tyr Cys Ala
        210                 215                 220

Arg Tyr Tyr Asp Asp His Tyr Cys Leu Asp Tyr Trp Gly Gln Gly Thr
```

```
                225                 230                 235                 240

Thr Val Thr Val Ser Ala Ser Thr Lys Gly Pro Glu Val Ser Ala
                    245                 250                 255

Leu Glu Lys Glu Val Ser Ala Leu Glu Lys Glu Val Ser Ala Leu Glu
                260                 265                 270

Lys Glu Val Ser Ala Leu Glu Lys
                275                 280

<210> SEQ ID NO 16
<211> LENGTH: 927
<212> TYPE: PRT
<213> ORGANISM: Artificial Sequence
<220> FEATURE:
<223> OTHER INFORMATION: Artificial Sequence constructed by rational
      design

<400> SEQUENCE: 16

Ala Ala Gly Cys Thr Gly Cys Cys Ala Cys Cys Ala Thr Gly Gly
1               5                   10                  15

Cys Cys Ala Thr Gly Thr Gly Thr Gly Gly Cys Gly Cys Cys Thr
                20                  25                  30

Gly Thr Gly Gly Thr Gly Gly Cys Thr Gly Cys Thr Gly Cys Thr Gly
            35                  40                  45

Cys Thr Gly Cys Thr Gly Cys Thr Gly Cys Thr Gly Cys Thr Gly Thr
        50                  55                  60

Gly Gly Cys Cys Cys Ala Thr Gly Gly Thr Gly Thr Gly Gly Gly Cys
65              70                  75                  80

Cys Gly Cys Cys Gly Cys Cys Gly Ala Cys Thr Ala Cys Ala Ala Ala
                85                  90                  95

Gly Ala Thr Gly Ala Thr Gly Ala Cys Gly Ala Thr Ala Ala Gly Cys
                100                 105                 110

Cys Gly Gly Thr Gly Cys Ala Gly Cys Thr Gly Gly Thr Gly Gly Ala
            115                 120                 125

Gly Thr Cys Thr Gly Gly Gly Gly Gly Ala Gly Gly Cys Thr Thr Gly
        130                 135                 140

Gly Thr Gly Cys Ala Gly Gly Cys Thr Gly Gly Gly Gly Ala Thr Thr
145                 150                 155                 160

Cys Thr Cys Thr Gly Ala Gly Ala Cys Thr Cys Thr Cys Cys Thr Gly
                165                 170                 175

Thr Gly Cys Thr Gly Cys Cys Thr Cys Thr Gly Gly Ala Cys Gly Cys
                180                 185                 190

Ala Cys Cys Thr Thr Cys Gly Gly Thr Ala Thr Thr Gly Gly Thr Ala
            195                 200                 205

Cys Cys Ala Thr Gly Gly Gly Cys Thr Gly Gly Thr Thr Cys Cys Gly
        210                 215                 220

Cys Cys Ala Ala Cys Cys Thr Cys Cys Ala Gly Gly Gly Ala Ala Gly
225                 230                 235                 240

Gly Ala Gly Cys Gly Thr Gly Ala Ala Thr Thr Gly Gly Thr Ala Gly
                245                 250                 255

Cys Ala Gly Cys Thr Ala Thr Thr Ala Gly Gly Thr Gly Gly Ala Gly
                260                 265                 270

Thr Ala Cys Thr Gly Gly Thr Gly Gly Cys Ala Cys Thr Cys Gly Cys
            275                 280                 285

Thr Ala Thr Gly Cys Ala Gly Ala Cys Thr Cys Cys Gly Thr Gly Ala
        290                 295                 300
```

-continued

```
Ala Gly Gly Gly Cys Cys Gly Ala Thr Thr Cys Ala Cys Cys Ala Thr
305                 310                 315                 320

Cys Thr Cys Cys Cys Gly Ala Gly Ala Cys Ala Ala Cys Gly Cys Cys
                325                 330                 335

Ala Ala Gly Cys Thr Cys Ala Cys Gly Gly Thr Ala Gly Ala Cys Cys
            340                 345                 350

Thr Gly Cys Ala Ala Ala Thr Gly Gly Ala Cys Ala Gly Cys Cys Thr
        355                 360                 365

Gly Ala Ala Ala Cys Cys Thr Gly Ala Ala Gly Ala Cys Ala Cys Gly
    370                 375                 380

Gly Cys Cys Gly Thr Thr Thr Ala Thr Thr Ala Cys Thr Gly Thr Gly
385                 390                 395                 400

Cys Ala Gly Cys Ala Gly Ala Thr Ala Gly Ala Cys Thr Gly Thr Cys
                405                 410                 415

Cys Cys Thr Thr Gly Ala Thr Thr Thr Ala Ala Gly Thr Gly Gly Thr
            420                 425                 430

Cys Gly Thr Thr Ala Cys Cys Ala Cys Thr Ala Cys Ala Ala Cys Cys
        435                 440                 445

Cys Cys Gly Cys Cys Gly Thr Gly Thr Ala Thr Gly Ala Cys Thr Ala
    450                 455                 460

Thr Thr Gly Gly Gly Gly Cys Cys Ala Gly Gly Gly Gly Ala Cys Cys
465                 470                 475                 480

Cys Ala Gly Gly Thr Cys Ala Cys Cys Gly Thr Cys Thr Cys Cys Thr
                485                 490                 495

Cys Ala Gly Gly Ala Gly Gly Thr Gly Gly Thr Gly Gly Cys Thr Cys
            500                 505                 510

Cys Cys Ala Ala Gly Thr Cys Cys Ala Ala Cys Thr Thr Cys Ala Gly
        515                 520                 525

Gly Ala Ala Thr Cys Cys Gly Gly Gly Gly Gly Thr Gly Gly Gly Cys
    530                 535                 540

Thr Gly Gly Thr Cys Cys Ala Gly Gly Cys Ala Gly Gly Cys Gly Gly
545                 550                 555                 560

Gly Thr Cys Cys Cys Thr Cys Cys Gly Cys Cys Thr Thr Ala Gly Cys
                565                 570                 575

Thr Gly Cys Gly Cys Ala Gly Cys Ala Thr Cys Cys Gly Gly Gly Cys
            580                 585                 590

Gly Cys Ala Cys Gly Thr Thr Thr Ala Gly Thr Ala Ala Cys Thr Ala
        595                 600                 605

Thr Cys Ala Cys Ala Thr Gly Gly Gly Ala Thr Gly Gly Thr Thr Cys
    610                 615                 620

Cys Gly Cys Cys Ala Gly Gly Cys Ala Cys Cys Cys Gly Gly Thr Ala
625                 630                 635                 640

Ala Ala Gly Ala Gly Cys Gly Gly Gly Ala Ala Thr Thr Gly Gly Thr
                645                 650                 655

Ala Gly Cys Cys Gly Cys Cys Ala Thr Ala Ala Gly Cys Gly Gly Thr
            660                 665                 670

Ala Gly Thr Gly Gly Ala Gly Gly Thr Thr Cys Ala Ala Cys Cys Thr
        675                 680                 685

Ala Thr Thr Ala Thr Ala Cys Cys Gly Ala Cys Ala Gly Thr Gly Thr
    690                 695                 700

Ala Ala Ala Gly Gly Gly Gly Cys Gly Ala Thr Thr Thr Ala Cys Ala
705                 710                 715                 720

Ala Thr Thr Thr Cys Ala Cys Gly Gly Ala Ala Thr Ala Ala Cys Gly
```

```
                    725                 730                 735
Cys Ala Ala Ala Gly Ala Ala Cys Ala Cys Ala Ala Thr Gly Thr Cys
                740                 745                 750

Ala Cys Thr Thr Cys Ala Ala Ala Thr Gly Thr Cys Ala Ala Ala Cys
            755                 760                 765

Cys Thr Cys Ala Ala Ala Cys Cys Thr Gly Ala Ala Gly Ala Cys Ala
        770                 775                 780

Cys Gly Gly Gly Thr Gly Thr Gly Thr Ala Thr Ala Thr Thr Gly
785                 790                 795                 800

Thr Ala Cys Cys Ala Cys Cys Cys Cys Ala Cys Gly Gly Ala Ala
            805                 810                 815

Ala Ala Ala Gly Gly Gly Thr Cys Ala Thr Cys Thr Ala Thr Cys Gly
                820                 825                 830

Ala Cys Thr Ala Thr Thr Gly Gly Gly Gly Cys Cys Ala Ala Gly Gly
            835                 840                 845

Ala Ala Cys Gly Cys Ala Ala Gly Thr Ala Ala Cys Ala Gly Thr Thr
        850                 855                 860

Ala Gly Cys Thr Cys Thr Gly Gly Thr Cys Gly Ala Thr Ala Cys Cys
865                 870                 875                 880

Cys Cys Thr Ala Thr Gly Ala Cys Gly Thr Thr Cys Cys Thr Gly Ala
            885                 890                 895

Cys Thr Ala Cys Cys Ala Thr Cys Ala Thr Cys Ala Cys Cys Ala Thr
        900                 905                 910

Cys Ala Thr Cys Ala Thr Thr Ala Gly Ala Gly Ala Thr Cys Thr
    915                 920                 925

<210> SEQ ID NO 17
<211> LENGTH: 1944
<212> TYPE: PRT
<213> ORGANISM: Artificial Sequence
<220> FEATURE:
<223> OTHER INFORMATION: Artificial Sequence constructed by rational
      design

<400> SEQUENCE: 17

Ala Ala Gly Cys Thr Thr Gly Cys Cys Ala Cys Ala Thr Gly Gly
1               5                  10                  15

Cys Cys Ala Thr Gly Thr Gly Gly Thr Gly Cys Gly Cys Cys Thr
            20                  25                  30

Gly Thr Gly Gly Thr Gly Gly Cys Thr Gly Cys Thr Gly Cys Thr Gly
        35                  40                  45

Cys Thr Gly Cys Thr Gly Cys Thr Gly Cys Thr Gly Cys Thr Gly Thr
    50                  55                  60

Gly Gly Cys Cys Ala Thr Gly Gly Thr Gly Gly Gly Gly Cys
65                  70                  75                  80

Cys Gly Cys Cys Gly Cys Cys Gly Ala Cys Thr Ala Cys Ala Ala Ala
                85                  90                  95

Gly Ala Thr Gly Ala Thr Gly Ala Cys Gly Ala Thr Ala Ala Gly Gly
            100                 105                 110

Ala Cys Ala Thr Thr Gly Thr Ala Cys Thr Gly Ala Cys Cys Cys Ala
        115                 120                 125

Gly Thr Cys Thr Cys Cys Ala Gly Cys Ala Ala Cys Thr Cys Thr Gly
    130                 135                 140

Thr Cys Thr Cys Thr Gly Thr Cys Thr Cys Cys Ala Gly Gly Gly Gly
145                 150                 155                 160
```

-continued

```
Ala Gly Cys Gly Thr Gly Cys Cys Ala Cys Cys Thr Gly Ala Gly
            165                 170                 175
Cys Thr Gly Cys Ala Gly Ala Gly Cys Cys Ala Gly Thr Cys Ala Ala
            180                 185                 190
Ala Gly Thr Gly Thr Ala Ala Gly Thr Thr Ala Cys Ala Thr Gly Ala
            195                 200                 205
Ala Cys Thr Gly Gly Thr Ala Cys Cys Ala Gly Cys Ala Gly Ala Ala
        210                 215                 220
Gly Cys Cys Gly Gly Cys Ala Ala Gly Gly Cys Ala Cys Cys
225                 230                 235                 240
Ala Ala Ala Ala Gly Ala Thr Gly Gly Ala Thr Thr Ala Thr Gly
                245                 250                 255
Ala Cys Ala Cys Ala Thr Cys Cys Ala Ala Gly Thr Gly Gly Cys
                260                 265                 270
Thr Thr Cys Thr Gly Gly Ala Gly Thr Cys Cys Cys Thr Gly Cys Thr
        275                 280                 285
Cys Gly Cys Thr Thr Cys Ala Gly Thr Gly Gly Cys Ala Gly Thr Gly
        290                 295                 300
Gly Gly Thr Cys Thr Gly Gly Ala Cys Cys Gly Ala Cys Thr Ala
305                 310                 315                 320
Cys Thr Cys Thr Cys Thr Cys Ala Cys Ala Ala Thr Cys Ala Ala Cys
                325                 330                 335
Ala Gly Cys Thr Thr Gly Ala Gly Gly Cys Thr Gly Ala Ala Gly
            340                 345                 350
Ala Thr Gly Cys Thr Gly Cys Cys Ala Cys Thr Thr Ala Thr Thr Ala
            355                 360                 365
Cys Thr Gly Cys Ala Ala Cys Ala Gly Thr Gly Gly Ala Gly Thr
        370                 375                 380
Ala Gly Thr Ala Ala Cys Cys Cys Gly Cys Thr Cys Ala Cys Gly Thr
385                 390                 395                 400
Thr Cys Gly Gly Thr Gly Cys Gly Gly Gly Ala Cys Cys Ala Ala
                405                 410                 415
Gly Gly Thr Gly Gly Ala Gly Ala Thr Cys Ala Ala Gly Gly Thr
            420                 425                 430
Gly Gly Thr Gly Gly Thr Gly Gly Thr Thr Cys Thr Gly Gly Cys Gly
            435                 440                 445
Gly Cys Gly Gly Cys Gly Gly Cys Thr Cys Cys Gly Gly Thr Gly Gly
        450                 455                 460
Thr Gly Gly Thr Gly Gly Thr Thr Cys Thr Cys Ala Gly Gly Thr Gly
465                 470                 475                 480
Cys Ala Ala Thr Thr Gly Gly Thr Gly Cys Ala Gly Thr Cys Thr Gly
                485                 490                 495
Gly Cys Gly Cys Thr Gly Ala Ala Gly Thr Ala Ala Gly Ala Ala
            500                 505                 510
Gly Cys Cys Thr Gly Gly Ala Gly Thr Cys Ala Gly Thr Gly
            515                 520                 525
Ala Ala Gly Gly Thr Cys Thr Cys Cys Thr Gly Cys Ala Ala Gly Gly
        530                 535                 540
Cys Thr Thr Cys Ala Gly Gly Ala Thr Ala Cys Gly Cys Cys Thr Thr
545                 550                 555                 560
Cys Ala Gly Cys Thr Ala Thr Cys Thr Gly Gly Ala Thr Cys
                565                 570                 575
Ala Ala Thr Thr Gly Gly Gly Thr Gly Cys Gly Gly Cys Ala Gly Gly
```

```
                580             585             590
Cys Gly Cys Cys Thr Gly Gly Ala Cys Ala Ala Gly Gly Cys Thr
        595             600             605
Cys Gly Ala Gly Thr Gly Gly Ala Thr Gly Gly Ala Cys Gly Gly
        610             615             620
Ala Thr Cys Thr Thr Thr Cys Cys Cys Gly Gly Cys Gly Ala Thr Gly
625                 630             635             640
Gly Gly Gly Ala Thr Ala Cys Thr Gly Ala Cys Thr Ala Cys Ala Ala
                645             650             655
Thr Gly Gly Gly Ala Ala Ala Thr Thr Cys Ala Ala Gly Gly Gly Cys
        660             665             670
Ala Gly Ala Gly Thr Cys Ala Cys Ala Ala Thr Thr Ala Cys Cys Gly
        675             680             685
Cys Cys Gly Ala Cys Ala Ala Thr Cys Cys Ala Cys Thr Ala Gly
        690             695             700
Cys Ala Cys Ala Gly Cys Cys Thr Ala Thr Gly Gly Ala Gly
705             710             715             720
Cys Thr Gly Ala Gly Cys Ala Gly Cys Cys Thr Gly Ala Gly Ala Thr
                725             730             735
Cys Cys Gly Ala Gly Ala Cys Ala Cys Gly Gly Cys Cys Gly Thr
        740             745             750
Gly Thr Ala Thr Thr Ala Cys Thr Gly Thr Gly Cys Ala Ala Gly Ala
        755             760             765
Ala Ala Thr Gly Thr Cys Thr Thr Thr Gly Ala Thr Gly Gly Thr Thr
770                 775             780
Ala Cys Thr Gly Gly Cys Thr Thr Gly Thr Thr Thr Ala Cys Thr Gly
785                 790             795             800
Gly Gly Gly Cys Cys Ala Gly Gly Gly Ala Ala Cys Cys Cys Thr Gly
                805             810             815
Gly Thr Cys Ala Cys Cys Gly Thr Cys Thr Cys Cys Thr Cys Gly
        820             825             830
Cys Cys Ala Gly Cys Ala Cys Ala Ala Gly Gly Gly Ala Cys Cys
        835             840             845
Thr Ala Ala Gly Gly Thr Gly Thr Cys Ala Gly Cys Thr Cys Thr
850             855             860
Ala Ala Gly Gly Ala Gly Ala Ala Gly Gly Thr Cys Thr Cys Thr Gly
865                 870             875             880
Cys Thr Cys Thr Thr Ala Ala Ala Gly Ala Ala Ala Ala Gly Thr
                885             890             895
Cys Thr Cys Ala Gly Cys Ala Cys Thr Gly Ala Ala Ala Gly Ala Gly
        900             905             910
Ala Ala Gly Gly Thr Thr Thr Cys Thr Gly Cys Ala Thr Thr Gly Ala
        915             920             925
Ala Gly Gly Ala Gly Cys Gly Gly Ala Gly Ala Ala Ala Gly Ala Gly
        930             935             940
Ala Gly Gly Cys Ala Gly Cys Gly Gly Cys Gly Ala Gly Gly Gly Ala
945                 950             955             960
Ala Gly Ala Gly Gly Ala Thr Cys Thr Cys Thr Gly Cys Thr Gly Ala
                965             970             975
Cys Ala Thr Gly Cys Gly Gly Cys Gly Ala Cys Gly Thr Gly Gly Ala
        980             985             990
Ala Gly Ala Gly Ala Ala Thr Cys  Cys Ala Gly Gly Ala  Cys Cys Thr
        995             1000            1005
```

-continued

```
Ala Thr Gly Thr Gly Gly Thr Gly Gly Cys Cys Cys Thr Gly
    1010                1015                1020

Thr Gly Gly Thr Gly Gly Cys Thr Gly Cys Thr Gly Cys Thr Gly
    1025                1030                1035

Cys Thr Gly Cys Thr Gly Cys Thr Gly Cys Thr Gly Cys Thr Gly
    1040                1045                1050

Thr Gly Gly Cys Cys Cys Ala Thr Gly Gly Thr Gly Thr Gly Gly
    1055                1060                1065

Gly Cys Cys Gly Cys Gly Cys Cys Gly Ala Thr Ala Thr Cys
    1070                1075                1080

Gly Thr Gly Ala Thr Gly Ala Cys Cys Cys Ala Gly Ala Cys Thr
    1085                1090                1095

Cys Cys Ala Cys Thr Cys Thr Cys Cys Cys Thr Gly Cys Cys Cys
    1100                1105                1110

Gly Thr Cys Ala Cys Cys Cys Thr Gly Gly Ala Gly Ala Gly
    1115                1120                1125

Cys Cys Cys Gly Cys Cys Ala Gly Cys Ala Thr Thr Ala Gly Cys
    1130                1135                1140

Thr Gly Cys Ala Gly Gly Thr Cys Thr Ala Gly Cys Ala Ala Gly
    1145                1150                1155

Ala Gly Cys Cys Thr Cys Thr Gly Cys Ala Cys Ala Gly Cys
    1160                1165                1170

Ala Ala Thr Gly Gly Cys Ala Thr Cys Ala Cys Thr Thr Ala Thr
    1175                1180                1185

Thr Thr Gly Thr Ala Thr Thr Gly Gly Thr Ala Cys Cys Thr Gly
    1190                1195                1200

Cys Ala Ala Ala Gly Cys Cys Ala Gly Gly Cys Ala Gly
    1205                1210                1215

Thr Cys Thr Cys Cys Ala Cys Ala Gly Cys Thr Cys Thr Gly
    1220                1225                1230

Ala Thr Thr Thr Ala Thr Cys Ala Ala Ala Thr Gly Thr Cys Cys
    1235                1240                1245

Ala Ala Cys Cys Thr Thr Gly Thr Cys Thr Cys Thr Gly Gly Cys
    1250                1255                1260

Gly Thr Cys Cys Cys Thr Gly Ala Cys Cys Gly Gly Thr Thr Cys
    1265                1270                1275

Thr Cys Ala Gly Gly Ala Thr Cys Cys Gly Gly Gly Thr Cys Ala
    1280                1285                1290

Gly Gly Cys Ala Cys Thr Gly Ala Thr Thr Thr Cys Ala Cys Ala
    1295                1300                1305

Cys Thr Gly Ala Ala Ala Ala Thr Cys Ala Gly Cys Ala Gly Gly
    1310                1315                1320

Gly Thr Gly Gly Ala Gly Gly Cys Thr Gly Ala Gly Gly Ala Thr
    1325                1330                1335

Gly Thr Thr Gly Gly Ala Gly Thr Thr Thr Ala Thr Thr Ala Cys
    1340                1345                1350

Thr Gly Cys Gly Cys Thr Cys Ala Gly Ala Ala Thr Cys Thr Ala
    1355                1360                1365

Gly Ala Ala Cys Thr Thr Cys Cys Thr Ala Cys Ala Cys Cys
    1370                1375                1380

Thr Thr Cys Gly Gly Cys Gly Gly Ala Gly Gly Gly Ala Cys Cys
    1385                1390                1395
```

```
Ala Ala Gly Gly Thr Gly Gly Ala Gly Ala Thr Cys Ala Ala Ala
    1400            1405                1410

Gly Gly Thr Gly Gly Thr Gly Gly Thr Gly Gly Thr Thr Cys Thr
    1415            1420                1425

Gly Gly Cys Gly Gly Cys Gly Gly Cys Gly Gly Cys Thr Cys Cys
    1430            1435                1440

Gly Gly Thr Gly Gly Thr Gly Gly Thr Gly Gly Thr Thr Cys Thr
    1445            1450                1455

Gly Ala Cys Gly Thr Cys Cys Ala Ala Cys Thr Gly Gly Thr Gly
    1460            1465                1470

Cys Ala Gly Thr Cys Ala Gly Gly Gly Cys Thr Gly Ala Ala
    1475            1480                1485

Gly Thr Gly Ala Ala Ala Ala Ala Cys Cys Thr Gly Gly Gly
    1490            1495                1500

Gly Cys Cys Thr Cys Ala Gly Thr Gly Ala Ala Gly Gly Thr Gly
    1505            1510                1515

Thr Cys Cys Thr Gly Cys Ala Ala Gly Gly Cys Thr Thr Cys Thr
    1520            1525                1530

Gly Gly Cys Thr Ala Cys Ala Cys Cys Thr Thr Thr Ala Cys Thr
    1535            1540                1545

Ala Gly Gly Thr Ala Cys Ala Cys Gly Ala Thr Gly Cys Ala Cys
    1550            1555                1560

Thr Gly Gly Gly Thr Ala Ala Gly Gly Cys Ala Gly Gly Cys Ala
    1565            1570                1575

Cys Cys Thr Gly Gly Ala Cys Ala Gly Gly Gly Thr Cys Thr Gly
    1580            1585                1590

Gly Ala Ala Thr Gly Gly Ala Thr Thr Gly Gly Ala Thr Ala Cys
    1595            1600                1605

Ala Thr Thr Ala Ala Thr Cys Cys Thr Ala Gly Cys Cys Gly Thr
    1610            1615                1620

Gly Gly Thr Thr Ala Thr Ala Cys Thr Ala Ala Thr Thr Ala Cys
    1625            1630                1635

Gly Cys Ala Gly Ala Cys Ala Gly Cys Gly Thr Cys Ala Ala Gly
    1640            1645                1650

Gly Gly Cys Cys Gly Cys Thr Thr Cys Ala Cys Ala Ala Thr Cys
    1655            1660                1665

Ala Cys Thr Ala Cys Ala Gly Ala Cys Ala Ala Ala Thr Cys Cys
    1670            1675                1680

Ala Cys Cys Ala Gly Cys Ala Cys Ala Gly Cys Cys Thr Ala Cys
    1685            1690                1695

Ala Thr Gly Gly Ala Ala Cys Thr Gly Ala Gly Cys Ala Gly Cys
    1700            1705                1710

Cys Thr Gly Cys Gly Thr Thr Cys Thr Gly Ala Gly Gly Ala Cys
    1715            1720                1725

Ala Cys Thr Gly Cys Ala Ala Cys Cys Thr Ala Thr Thr Ala Cys
    1730            1735                1740

Thr Gly Thr Gly Cys Ala Ala Gly Ala Thr Ala Thr Thr Ala Thr
    1745            1750                1755

Gly Ala Thr Gly Ala Thr Cys Ala Thr Thr Ala Cys Thr Gly Cys
    1760            1765                1770

Cys Thr Thr Gly Ala Cys Thr Ala Cys Thr Gly Gly Gly Gly Cys
    1775            1780                1785

Cys Ala Ala Gly Gly Cys Ala Cys Cys Ala Cys Gly Gly Thr Cys
```

-continued

```
                1790                1795                1800

Ala Cys Cys Gly Thr Cys Thr Cys Cys Thr Cys Ala Gly Cys Cys
                1805                1810                1815

Ala Gly Cys Ala Cys Ala Ala Ala Gly Gly Ala Cys Cys Thr
                1820                1825                1830

Gly Ala Gly Gly Thr Thr Ala Gly Thr Gly Cys Ala Thr Thr Gly
                1835                1840                1845

Gly Ala Gly Ala Ala Ala Gly Ala Ala Gly Thr Ala Ala Gly Cys
                1850                1855                1860

Gly Cys Ala Thr Thr Gly Gly Ala Ala Ala Ala Gly Ala Ala
                1865                1870                1875

Gly Thr Gly Thr Cys Thr Gly Cys Ala Thr Thr Gly Gly Ala Gly
                1880                1885                1890

Ala Ala Ala Gly Ala Gly Gly Thr Cys Thr Cys Cys Gly Cys Gly
                1895                1900                1905

Cys Thr Cys Gly Ala Ala Ala Ala Gly Cys Ala Thr Cys Ala Thr
                1910                1915                1920

Cys Ala Cys Cys Ala Thr Cys Ala Thr Cys Ala Thr Thr Ala Ala
                1925                1930                1935

Ala Gly Ala Thr Cys Thr
                1940
```